US007164016B2

(12) United States Patent
Platzek et al.

(10) Patent No.: US 7,164,016 B2
(45) Date of Patent: Jan. 16, 2007

(54) MACROCYCLIC METAL COMPLEXES AND THEIR USE FOR THE PRODUCTION OF CONJUGATES WITH BIOMOLECULES

(75) Inventors: Johannes Platzek, Berlin (DE); Heribert Schmitt-Willich, Berlin (DE); Günther Michl, Rüdersdorf (DE); Thomas Frenzel, Berlin (DE); Detlev Sülzle, Berlin (DE); Hans Bauer, Berlin (DE); Bernd Radüchel, Berlin (DE); Hanns-Joachim Weinmann, Berlin (DE); Heiko Schirmer, Berlin (DE)

(73) Assignee: Schering AG, Berlin (DE)

( * ) Notice: Subject to any disclaimer, the term of this patent is extended or adjusted under 35 U.S.C. 154(b) by 120 days.

(21) Appl. No.: 10/198,046

(22) Filed: Jul. 19, 2002

(65) Prior Publication Data

US 2003/0108486 A1     Jun. 12, 2003

(30) Foreign Application Priority Data

Jul. 20, 2001   (DE) ................................ 101 35 356

(51) Int. Cl.
   *C07D 257/02*  (2006.01)
(52) U.S. Cl. .................................... 540/474
(58) Field of Classification Search ................. 540/474
   See application file for complete search history.

(56) References Cited

U.S. PATENT DOCUMENTS

| 5,006,643 | A |   | 4/1991  | Fazio et al. ................ 574/10 |
| 5,049,667 | A | * | 9/1991  | Schaefer et al. ........... 540/474 |
| 5,132,409 | A | * | 7/1992  | Felder et al. ................ 534/10 |
| 5,811,077 | A | * | 9/1998  | Seri et al. ................ 424/9.363 |
| 5,972,307 | A |   | 10/1999 | Carvalho et al. .......... 424/1.65 |
| 6,063,361 | A |   | 5/2000  | Schmitt-Willich et al. |

FOREIGN PATENT DOCUMENTS

| DE | 19603033    | 7/1997  |
| EP | 0 565 930   | 10/1993 |
| WO | 89/01476    | 2/1989  |
| WO | WO 97/02051 | 1/1997  |
| WO | 01/52900    | 7/2001  |

OTHER PUBLICATIONS

Kang et al. (Inorganic Chemistry (1993), 32(13), 2912-18. Abstract.*
Lowe et al. (Journal of the American Society (2001), 123(31), 7601-7609).*
Lowe et al. (Inorganica Chimica Acta (2001), 317(1,2), 163-173). Abstarct.*
Hashiguchi et al. (Nippon Kagaku Kaishi (1993), (5), 521-7). Abstract.*

J. Chem. Soc., Chem. Commun., 1989—XP-001031170, pp. 797-798, Synthesis of a Kinetically Stable Yttrium-90 Labelled Macrocycle-Antibody Conjugate, Jonathan P.L. Cox et al.
Tetrahedron Letters, vol. 37, No. 42, pp. 7515-7518, 1996, A Convenient, Novel Approach for the Synthesis of Polyaza Macrocyclic Bifunctional Chelating Agents, Anil Kumar Mishra et al.
Bioorganic & Medicinal Chemistry Letters 8 (1998) 1207-1210, Direct Synthesis of [DOTA-DPhe$^1$,Tyr$^3$]-Octreotide (SMT 487): Two Conjugates for Systemic Delivery of Radiotherapeutical Nuclides to Somatostatin Receptor Positive TUmors in Man, Rainer Albert et al.
J. Am. Chem. Soc. 1999, 121, 1413-1414, XP-002115324, A Calcium-Sensitive Magnetic Resonance Imaging Contrast Agent.
Wiley-VCH Verlag GmbH, D-69451 Weinheim, 1999, Chem. Eur J 1999.5.No. 7 pp. 1974-1981, XP-000829499, Radiometal-Labelled Macrocyclic Chelator-Derivatised Somatostatin Analogue with Superb Tumour-Targeting Properties and Potential for Receptor-Mediated Internal Radiotherapy, A. Heppeler et al.
J. Chem. Soc. Perkin Trans. 2 1993, pp. 605-620, XP-002146570, Synthesis of Charged and Uncharged Complexes of Gadolinium and Yttrium with Cyclic Polyazaphosphinic Acid Ligands for in vivo Applications, Kanthi P. Pulukkody et al.
Tetrahedron Letters, vol. 34, No. 35, pp. 5531-5534, 1993, XP-001042259, A New Synthetic Route to 2-(Nitrobenzyl)-1,4,7,10-Tetraazacyclododecane, Martha L.. Garrity et al.
Chem. Eur. J. 2000, 6. No. 14, Wiley-VCH Verlag GmbH, D-69451 Weinheim, 2000, XP-002220623, Non-covalent Conjugates between Cationic Polyamino Acids and Gd$^{III}$ Chelates: A Route for Seeking Accumulation of MRI-Contrast Agents at Tumor Targeting Sites, Silvio Aime et al.
Bioorganic & Medicinal Chemistry 7 (1999) 2313-2320, XP-002220624, Improved Synthesis of the Bifunctional Chelating Agent 1,4,7,10-Tetraaza-N-(1-carboxy-3-(4-nitrophenyl)propyl)-N',N'',N'''-tris(acetic acid)cyclododecane (PA-DOTA), Lara L. Chappell et al.
Chem. Eur. J. 2001, 7, No. 1, pp. 64-71, XP-002220625, Inulin as a Carrier for Contrast Agents in Magnetic Resonance Imaging, Daniele M. Corsi et al.
J. Chem. Soc., Perkin Trans. 2, 2000, 1819-1831, XP-002220626, A model system using modulation of lanthanide luminescence to signal $Zn^{2+}$ in competitive aqueous media, Ofer Reany et al.
J. Chem. Soc., Perkin Trans. 2, 2000, 1281-1283, XP-002220627, The efficient intramolecular sensitization of terbium(III) and europium(III) by benzophenone-containing ligands, Andrew Beeby et al.
J. Chem. Soc., Perkin Trans. 2, 2001, 929-933, XP-002220628, Gadolinium DO3A derivatives mimicking phospholipids; preparation and in vitro evaluation as pH responsive MRI contrast agents, Ragnar Hovland et al.

(Continued)

*Primary Examiner*—Bruck Kifle
(74) *Attorney, Agent, or Firm*—Millen, White, Zelano & Branigan, P.C.

(57) ABSTRACT

The invention relates to macrocyclic metal complexes and their production and use for the production of conjugates with biomolecules. The conjugates are suitable as contrast media in NMR diagnosis and radiodiagnosis as well as for radiotherapy. High relaxivity is achieved by a special liganding of macrocyclic compounds, and a fine-tuning of the relaxivity is made possible.

23 Claims, No Drawings

OTHER PUBLICATIONS

J. Chem. Soc. Perkin Trans. 1, 1990 pp. 2567-2576, XP-001119344, Synthesis of C- and N-Functionalised Derivatives of 1,4,7-Triazacyclonon-ane-1,4,7-triyltriacetic acid (NOTA), 1,4,7,10-Tetra-0azacyclododecane-1,4,7,10-tetrayltetra-acetic Acid (DOTA), and Dlethylenenetriaminepenta-acetic Acid (DTPA): Bifunctional Complexing Agents for the Derivatisation of Antibodies, Jonathan P.L. Cox et al.

Journal of Pharmaceutical Sciences / vol. 82, No. 5, May 1993 pp. 425-479, XP-001119429, A Specific Radioimmunoassay for the Measurement of Gadoteridol, a Contrast Agent for Magnetic Resonance Imaging in Biological Fluids, Marc D. Ogan et al.

Symposium Abstracts, pp. 512-514, XP-001119556, Synthesis Of A DOTA Conjugated Peptide And Its Labeling With Ce-141, John R. Grierson et al.

Symposium Abstracts, J. Labelled Cpd. Radiopharm 44. Suppl. 1 (2001) pp. S814-S816, XP-001119526, Synthesis And Isolation Of Active Esters Of DOTA, W. Mier et al.

J. Chem. Soc. Dalton Trans., 1996, pp. 2347-2350, XP-001119339, Selectivity of macrocyclic aminocarboxylates for alkaline-earth metal ions and stability of their complexes, C. Allen Chang.

Synthetic Communications, 26(8), 1595-1603 (1996), XP-001119430, One Stage Monosubstitution in Cyclen-Two Novel Examples, A.A. Formanovsky et al.

Gazzetta Chimica Italiana, 126, 1996—Published by Societa Chimica Italiana, XP-001119427, A New Approach To Hepatospecific MRI Contrast Agents: Gadolinium Complexes Conjugated To Iodinated Synthons (*), Pier Lucio Anelli et al.

Chem. Commun. 2000, 473-474, XP-002220629, Selective signaling of zinc ions by modulation of terbium luminescence, Ofer Reany et al.

J. AM. Chem. Soc. 1995, 117, 8132-8138, XP-002220630, Luminescent Polyaminocarboxylate Chelates of Terbium and Europium: The Effect of Chelate Structure, Min Li et al.

Peter Caravan et al., "Gadolinium(III) Chelates as MRI Contrast Agents: Structure, Dynamics, and Applications", *Chem. Rev. 1999*. vol. 99, No. 9, pp. 2293-2352

J. Am. Chem. Soc. 2001, 123, 7601-7609 - XP-001147822, pH-Dependent Modulation of Relaxivity and Luminescence in Macrocyclic Gadolinium and Europium Complexes Based on Reversible Intramolecular Sulfonamide Ligation, Mark P. Lowe et al.

XP-001042289, Inorganica Chimica Acts 317 (2001) 163-173 - pH Switched sensitization of europium(III) by a dansyl group, Mark P. Lowe et al.

J. Am. Chem. Soc. 2000, 122, 9781-9792 - XP009058154, Correleation of Water Rate with Isomeric Composition in Diastereoisomeric Gadolinium Complexes of Tetra(carboxyethyl)dota and Related Macrocyclic Ligands, Mark Woods et al.

Inorg. Chem. 1993, 32, 2912-2918 - XP009058169, Synthesis, Characterization, and Crystal Structure of the Gadolinium(III) Chelate of (1R,4R,7R)-a,a',a"- Trimethyl- 1, 4, 7, 10-tetraazacyclododecane-1, 4, 7-triacetic Acid (DO3MA), Sang I. Kang et al.

Vol. 17 1996 - Chemical Journal Of Chinese Universities - XP009058156 No. 8, 1179-1181, Na[Ln(DOTMA)(H$_2$O)] - 2H$_2$O with Abstract (Synthesis and Characterization of Rare Earth Complex with Polyaza Polycarboxylic Macrocycle Na[Ln(DOTMA)(H$_2$O] - 2H$_2$O, Chen De-Fu et al.

* cited by examiner

MACROCYCLIC METAL COMPLEXES AND THEIR USE FOR THE PRODUCTION OF CONJUGATES WITH BIOMOLECULES

The invention relates to the subjects that are characterized in the claims, i.e., macrocyclic metal complexes as well as their use for the production of conjugates with biomolecules. The conjugates are suitable for the production of contrast media for NMR diagnosis and radiodiagnosis as well as agents for radiotherapy.

A prerequisite for a specific and successful therapy is an exact diagnosis. Specifically in the diagnostic field, the possibilities have very greatly increased in recent years, whereby, for example, NMR diagnosis is able to visualize virtually any anatomical detail selectively and with great accuracy. In many cases, the corresponding structures are visible only by the application of contrast media, however. Moreover, the possibility exists of configuring the contrast media in such a way that they selectively accumulate in the desired target structures. To this end, the accuracy of the imaging can be increased with simultaneous reduction of the required amount of contrast medium.

As contrast media for NMR diagnosis, chelate complexes of paramagnetic metals are suitable. The theory and application of gadolinium(III) chelates as NMR contrast media are explained in detail in a survey article by P. Caravan et al. in Chem. Rev. 1999, 99, 2293–2352.

The image intensity in the proton NMR is basically determined by the water protons. It depends on the nuclear relaxation times. Complexes of paramagnetic transition metals and lanthanoids shorten the relaxation times of adjacent protons by dipolar interactions. The paramagnetic contrast media are not directly detected, but rather an indirect detection is carried out based on the fact that the contrast media can change relaxation times of adjacent protons, such as water protons. Based on their high magnetic moments and relaxation efficiency, $Gd^{3+}$, $Fe^{3+}$ and $Mn^{2+}$ are preferred paramagnetic metal cations in NMR diagnosis.

An important physical value, which describes the relaxation behavior of protons, is longitudinal relaxation time $T_1$. Tissues with short relaxation times $T_1$ generally yield images of higher intensity than those with longer relaxation times. If the reciprocal value of measured relaxation time $T_1$ based on concentration c is applied to a specific paramagnetic ion, straight lines of rise R are obtained. This rise is also named relaxivity, which is a measurement of the capacity of the corresponding paramagnetic ion to shorten the relaxation time of the adjacent protons.

The use of radiopharmaceutical agents for diagnostic and therapeutic purposes has also been known for a long time in the area of biological and medical research. In particular, radiopharmaceutical agents are used to visualize specific structures such as, for example, the skeleton, organs or tissues. The diagnostic application requires the use of such radioactive agents, which accumulate after administration specifically in the structures in patients that are to be examined. These locally accumulating radioactive agents can then be traced, plotted or scintigraphed using suitable detectors, such as, for example scintillation cameras or other suitable recording processes. The dispersion and relative intensity of the detected radioactive agent identifies the site of a structure in which the radioactive agent is found and can visualize the presence of anomalies in structures and functions, pathological changes, etc.

Radiopharmaceutical agents can be used in a similar way as therapeutic agents to irradiate pathological tissues or areas. Such treatment requires the production of radioactive therapeutic agents that accumulate in certain structures, organs or tissues.

Because of their sometimes relatively high toxicity, the required ions are normally not administered in the form of water-soluble salts, but rather in the form of chelate complexes. The latter can be eliminated virtually unchanged from the body. The smaller the complexes in solution are, the lower is their moment of inertia and the faster they rotate in solution (Tumbling Motion Time). The faster a complex rotates, the lower its relaxivity is. The relaxivity thus increases with the molecular mass of the entire complex. A high molecular mass can be achieved by binding to macromolecules. A good NMR contrast medium is distinguished, i.a., in that it has a large value for the relaxivity.

Conjugates of Gd-DTPA (diethylenetriaminepentaacetic acid) with albumin are described by, for example, M. D. Organ et al. in Invest. Radiol. 1987, 22, 665–671 and U. Schmiedl et al. in Radiology 1987, 162, 205–210. Conjugates of macrocyclic metal complexes and biomolecules are disclosed in WO 95/31444. To improve the selectivity of contrast media, WO 01/08712 proposes a contrast medium that comprises at least two metal chelate units as image-improving groups and at least two "target binding units" for binding the contrast medium molecule to the desired target molecule or target organ in the body.

Large contrast medium molecules with high molar mass are obtained according to WO 97/02051 by incorporation of macrocyclic metal complexes in cascade polymers.

Tetraazacyclododecanetetraacetic acid derivatives of high stability and good solubility based on deficient charge that are suitable for binding to biomolecules are described in EP-A-0 565 930.

The binding of macrocyclic metal complexes to biomolecules that is described above makes possible both an increase of relaxivity and selectivity of the contrast medium. The higher the relaxivity of the contrast medium, the smaller amount of contrast medium must be administered to the patient and the greater the opacification in the image. For this reason, it is additionally desirable to make available NMR contrast media with the highest possible relaxivity.

An object of this invention thus consists in making available improved contrast media for NMR diagnosis and radiodiagnosis as well as agents for radiotherapy. In particular, these NMR contrast media are to have as high a relaxivity as possible and are to accumulate as selectively as possible at a desired site in the body.

It has now been found that this object can be achieved, surprisingly enough, in that a 1,4,7,10-tetraazacyclododecane macrocyclic compound with special ligands is provided. The new qualities of the compounds according to the invention are evident if they are bonded to biomolecules. By the special ligating of the macrocyclic compound, the relaxivity of the contrast medium that is obtained is increased, and in addition a fine-tuning of the relaxivity for a desired use is possible.

This invention thus relates to compounds of formula I

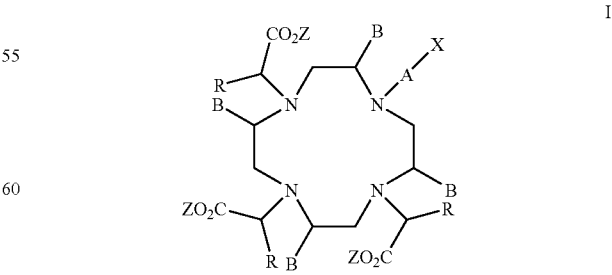

in which
Z represents a hydrogen atom or at least two Z's represent a metal ion equivalent, B represents a hydrogen atom or a $C_{1-4}$-alkyl radical, R represents a hydrogen atom or a straight, branched or cyclic, saturated or unsaturated $C_{1-10}$-alkyl or aryl radical, which optionally is substituted with a carboxyl group —$SO_3H$ or —$PO_3H_2$, and whereby the alkyl chain of the $C_{1-10}$-alkyl radical optionally contains an aryl group and/or 1–2 oxygen atoms, provided that radicals B and R do not both represent hydrogen atoms simultaneously, A represents a straight or branched, saturated or unsaturated $C_{1-30}$-hydrocarbon chain that optionally contains 1–5 oxygen atoms, 1–5 nitrogen atoms and/or 1–5 —NR' radicals, in which R' is defined as R, but can be selected independently, which optionally is substituted with 1–3 carboxyl groups, 1–3 —$SO_3H$, 1–3 —$PO_3H_2$ and/or 1–3 halogen atoms, in which optionally 1–3 carbon atoms are present as carbonyl groups, whereby the chain or a portion of the chain can be arranged concentrically, and which is configured in such a way that X is connected via at least 3 atoms to the nitrogen to which A is bonded, and X represents a group that can participate in a reaction with a biomolecule, as well as their salts and their use for the production of a conjugate with a biomolecule.

A corresponding macrocyclic compound in which the four nitrogen atoms of the macrocyclic ring are substituted in each case with the substituent —$CH(CO_2H)CH_2CH_2$—$CO_2H$ is disclosed in P. Caravan et al., Chem. Rev. 1999, 99, 2293–2352. A possible use of this compound for the production of conjugates with biomolecules is not disclosed, however. WO 97/02051 discloses macrocyclic compounds, in which A is a radical —$CH(R^4)$—CO—$NR^2$—$U^6$, as intermediate compounds for the production of cascade polymers. EP-A-0-565 930 discloses macrocyclic compounds, in which A is a radical —$CH(R_3)$—C(O)—NH—$(CH_2)_{1-6}$—NH—D—. An increase in relaxivity by certain substituents is not disclosed. These compounds are consequently excluded in the definition of the compound of formula I in claim 1.

Unless otherwise indicated, "alkyl radical" is defined here as a saturated or unsaturated, straight-chain or branched or cyclic alkyl radical with the indicated number of carbon atoms. If this radical can contain other groups or atoms, it is understood here that the other groups or atoms in addition to the already existing atoms of the radical are present and can be introduced at any position of the radical including the terminal positions.

"Aryl" is defined here preferably as phenyl, bisphenyl, pyridyl, furanyl, pyrrolyl and imidazolyl. Especially preferred is phenyl.

"Hydrocarbon chain," which can be arranged completely or partially concentrically, is defined here preferably as a hydrocarbon chain such as, for example, an alkyl chain, which can comprise, for example, an aliphatic or aromatic, optionally heterocyclic 5- or 6-ring (e.g., phenyl(ene), pyridyl(ene) or cyclohexyl(ene)) or consists of the latter.

In the compound of formula I according to the invention, three of the four nitrogen atoms of the macrocyclic ring are substituted with optionally substituted acetic acid or carboxylate methyl radicals. These radicals contribute to the coordination or to the charge equalization of a coordinated metal ion. Z therefore stands either for a hydrogen atom or a metal ion equivalent.

The acetic acid or carboxylate methyl radicals at three of the nitrogen atoms of the macrocyclic ring in addition can have a substituent R. Moreover, the macrocyclic ring can have another substituent B at four of its carbon atoms. A special feature of the compounds according to the invention consists in that B and R cannot represent hydrogen atoms simultaneously, i.e., the macrocyclic ring must have additional substituents either directly on its ring atoms and/or on the acetic acid or carboxylate methyl substituents of its nitrogen atoms. By the suitable selection of these additional substituents, the desired fine-tuning of the relaxivity of a contrast medium that is produced with use of the compound according to the invention is carried out.

B can be a hydrogen atom or a $C_{1-4}$-alkyl radical. Preferred $C_{1-4}$-alkyl radicals are methyl, ethyl and iso-propyl.

If B is a hydrogen atom in the compounds of formula I according to the invention, R stands for a straight, branched and/or cyclic, saturated or unsaturated $C_{1-10}$-alkyl (preferably $C_{5-10}$-alkyl) or aryl radical, which optionally is substituted with a carboxyl group, —$SO_3H$ or —$PO_3H_2$, and whereby the alkyl chain of the $C_{1-10}$-alkyl radical optionally contains an aryl group and/or 1–2 oxygen atoms. As alkyl radicals, straight-chain or branched, preferably saturated $C_{1-10}$- and especially $C_{1-4}$-alkyl radicals, such as methyl, ethyl, n-propyl, iso-propyl, n-butyl, iso-butyl and tert-butyl, as well as cyclohexyl, are preferred. As an alternative, straight-chain, branched or cyclic, preferably saturated $C_{5-10}$-alkyl radicals, such as pentyl, hexyl, cyclohexyl, heptyl, octyl, nonyl and decyl, are preferred. The $C_{1-10}$-alkyl radical for R can optionally be substituted with a carboxyl group, —$SO_3H$ or —$PO_3H_2$. Preferred examples of such substituted alkyl groups are —$CH_2$—COOH and —$C(CH_3)_2$—COOH. Moreover, the alkyl chain of the $C_{1-10}$-alkyl radical can contain an aryl group and/or 1–2 oxygen atoms. The aryl group and the oxygen atoms can be present at any position within the alkyl chain. The aryl group, moreover, can also be arranged in terminal position on the alkyl chain and can form an aryloxy group together with an oxygen atom. Especially a phenyl group is suitable as an aryl group.

A preferred alkyl chain for R, which optionally contains an aryl group and 1–2 oxygen atoms, is a radical of formula —$(CH_2)_m$—$(O)_n$-(phenylene)$_p$—Y, in which m is an integer from 1–5, n is 0 or 1, p is 0 or 1 and Y is a hydrogen atom, a methoxy radical, a carboxyl group, —$SO_3H$ or —$PO_3H_2$. Substituent Y is preferably in para-position in this case.

The aryl radical for R is preferably a phenyl radical, which is optionally substituted with a carboxyl group, —$SO_3H$ or —$PO_3H_2$.

If B is a hydrogen atom, R preferably stands for isopropyl, isobutyl, tert-butyl, a straight-chain or branched $C_{5-10}$-alkyl radical, cyclohexyl, —$CH_2$—COOH, —$C(CH_3)_2$—COOH, a phenyl radical or a radical of formula —$(CH_2)_m$—$(O)_n$-(phenylene)$_p$—Y, in which m is an integer from 1 to 5, n is 0 or 1, p is 0 or 1, and Y represents a hydrogen atom, a methoxy radical, a carboxyl group, —$SO_3H$ or —$PO_3H_2$, and R especially preferably stands for isopropyl, cyclohexyl or phenyl.

The substituted macrocyclic ring of the compound of formula I can be bonded via a spacer A to a biomolecule using a group X, which can participate in a reaction with a biomolecule.

In this case, spacer A represents a straight or branched, saturated or unsaturated $C_{1-30}$ hydrocarbon chain, which optionally contains 1–5 oxygen atoms, 1–5 nitrogen atoms and/or 1–5 —NR' radicals, in which R' is defined as R above but can be selected independently, which optionally is substituted with 1–3 carboxyl groups, 1–3 —$SO_3H$, 1–3 —$PO_3H_2$ and/or 1–3 halogen atoms, in which optionally 1–3 carbon atoms are present as carbonyl groups, whereby the chain or a portion of the chain can be arranged concentrically and which is configured in such a way that X is connected via at least 3 atoms to the nitrogen atom to which A is bonded.

The spacer is to have at least three atoms and preferably at least four atoms in a chain between the nitrogen atom of the macrocyclic ring and X. A chain of atoms is defined in this case as the shortest connection between the nitrogen atom of the macrocyclic ring and X via a ring as well. In terms of this definition, for example, a para-phenylene group would be regarded as a spacer with four atoms in a chain, and a meta-phenylene group would be regarded as a spacer with three atoms in a chain. In determining the length of the atom chain, carbon, nitrogen and oxygen atoms are simultaneously counted in each case as an atom. Substituents in these atoms or side chains are not part of the number of atoms inside the chain.

—A—X is preferably selected to be different from the substituent —CH(R)—CO$_2$Z.

Spacer A preferably can be represented as a radical A'—U, in which A' is bonded to the nitrogen atom of the macrocyclic ring and U is bonded to X. Hereinafter, A' is preferably a) a bond,
b) —CH(CO$_2$H)—,
c) a group of formula

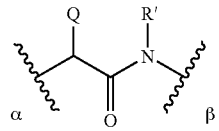

in which Q represents a hydrogen atom, a $C_{1-10}$-alkyl radical, which optionally is substituted with a carboxyl group, or Q represents an aryl radical, which optionally is substituted with a carboxyl group, a $C_{1-15}$-alkoxy group, an aryloxy group or a halogen atom, and R' is defined as R, but can be selected independently, or d) a group of formula

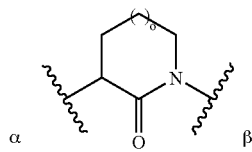

in which o is 0 or 1, and the ring optionally is annellated with a benzene ring, whereby this benzene ring, if present, can be substituted with a methoxy or carboxyl group, —SO$_3$H or —PO$_3$H$_2$. In the groups above under c) and d), the positions that are marked

are bonded to the adjacent groups, position α is bonded to a nitrogen atom of the macrocyclic ring, and position β is bonded to U.

In the group of formula

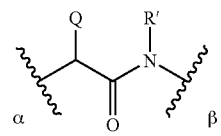

Q is preferably a linear or branched $C_{1-10}$ radical, especially a $C_{1-4}$-alkyl radical, such as methyl, ethyl or isopropyl, or a cyclohexyl radical. These radicals can optionally be substituted with a carboxyl group, whereby a carboxymethyl radical is preferred. The preferred aryl radical for Q is phenyl. This aryl radical can be substituted with a carboxyl group, a $C_{1-15}$-alkoxy group, an aryloxy group, such as especially a phenoxy group, or a halogen atom, such as fluorine, chlorine, bromine or iodine, and especially fluorine or chlorine. If the aryl radical is a phenyl radical, the latter is preferably substituted in para-position with one of the above-mentioned groups. Especially preferred groups for Q are methyl, phenyl and p-dodecanoxyphenyl.

R' is defined as R above, but can be selected independently from R. R' is especially preferably a hydrogen atom.

A' is preferably selected from a bond, —CH(CO$_2$H)—, —C(CH$_3$)H—CO—NH—, —C(phenyl)H—CO—NH—, —C(p-dodecanoxyphenyl)H—CO—NH—,

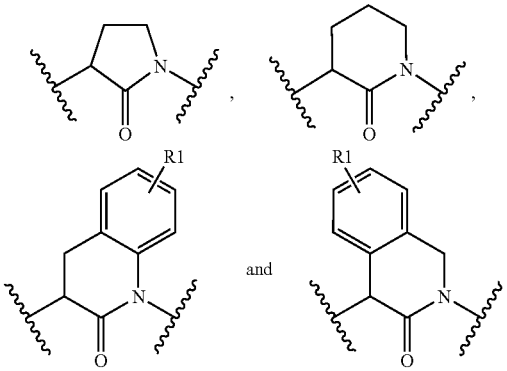

and in which R$^1$ is —OCH$_3$, —CO$_2$H, —SO$_3$H or —PO$_3$H$_2$.

If spacer A is represented as a radical A'—U, and A' has the meaning defined above, U is preferably a straight or branched, saturated or unsaturated $C_{1-30}$-hydrocarbon chain, which optionally contains 1–3 oxygen atoms, 1–3 nitrogen atoms and/or 1–3 —NR" radicals, in which R" is defined as R above, but can be selected independently, and in which optionally 1–3 carbon atoms are present as carbonyl groups, whereby the chain or a portion of the chain can be arranged concentrically. U is especially preferably an aryl radical or a $C_{1-20}$-alkyl radical (preferably straight-lined or at least partially cyclic and saturated) that optionally contains 1–3 oxygen atoms, 1–3 NR" radicals, 1–2 phenylene radicals and/or a pyridylene radical, in which optionally 1–3 carbon atoms are present as carbonyl groups, and which optionally is substituted with an aryl radical (e.g., phenyl). A' and U together must be configured in such a way that X is connected by at least three atoms to the nitrogen atom to which A' is bonded. The chain of at least three atoms is defined as above in A.

The aryl radical for U is preferably a phenyl radical. The $C_{1-20}$-alkyl radical for U is preferably a linear, saturated $C_{1-10}$-alkyl radical, cyclohexyl radical or cyclohexyl-$C_{1-5}$-alkyl radical. The alkyl radicals of these radicals can optionally be interrupted by 1 oxygen atom, 1 phenylene radical and/or 1 pyridylene radical or can contain a —CO—NR'' radical or can be substituted with phenyl. U is preferably selected from —$CH_2$—, —$(CH_2)_5$—, —$(CH_2)_{10}$—, -phenylene-O—$CH_2$—, -phenylene-O—$(CH_2)_3$—, -phenylene-O—$(CH_2)_{10}$—, —$CH_2$-phenylene-, -cyclohexylene-O—$CH_2$—, -phenylene-, —C(phenyl)H—, —$CH_2$-pyridylene-O—$CH_2$- and —$CH_2$—CO—NH—$CH_2$—$CH_2$—. In the above-mentioned preferred groups for U, the phenylene groups are preferably substituted in para-position, and the pyridylene groups are preferably pyrid-2,5-ylene groups or pyrid-2,4-ylene groups.

Preferred groups for the spacer A are:

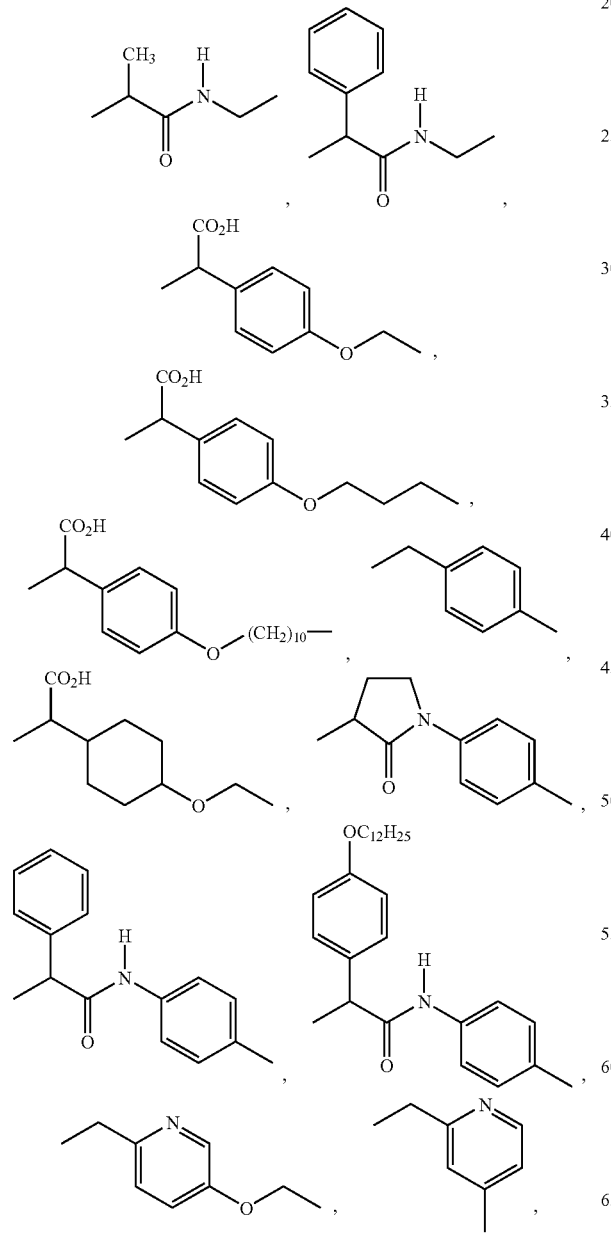

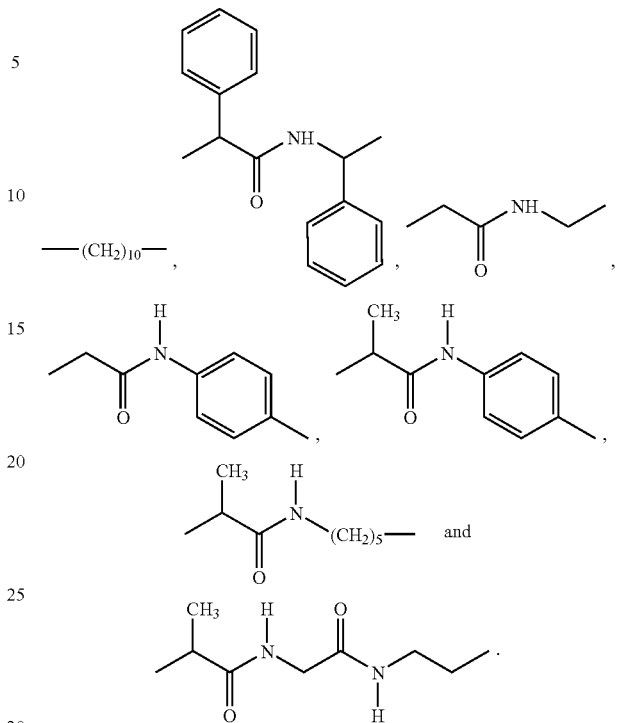

Via spacer A, a group X is bonded to the macrocyclic ring in the compounds of formula I. This group X is a group that can participate in a reaction with a biomolecule. For this purpose, for example, carboxyl (—COOH), activated carboxyl, amino (—$NH_2$), isocyanate (—NCO), isothiocyanate (—NCS), hydrazine (—$NHNH_2$), semicarbazide (—NH-CONH$NH_2$), thiosemicarbazide (—NHCSNH$NH_2$), chloroacetamide (—NHCOCH$_2$Cl), bromoacetamide (—NHCOCH$_2$Br), iodoacetamide (—NHCOCH$_2$I), acylamino, such as, for example acetylamino (—NHCOCH$_3$), mixed anhydrides, azide, hydroxide, sulfonyl chloride, carbodiimide or a group of formulas

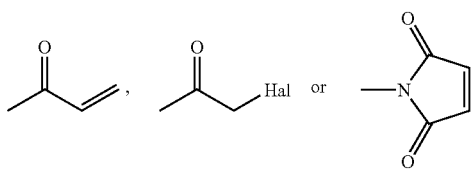

in which Hal represents a halogen atom, is suitable.

Activated carboxyl groups are defined above as those carboxyl groups that can be derivatized in such a way that they facilitate the reaction with a biomolecule. Which groups can be used for activation is known, and reference can be made to, for example, M. and A. Bodanszky, "The Practice of Peptide Synthesis," Springerverlag 1984. Examples are adducts of carboxylic acid with carbodiimides or activated esters, such as, e.g., hydroxybenzotriazole esters. Especially preferred is the activated carboxyl group for X that is selected from

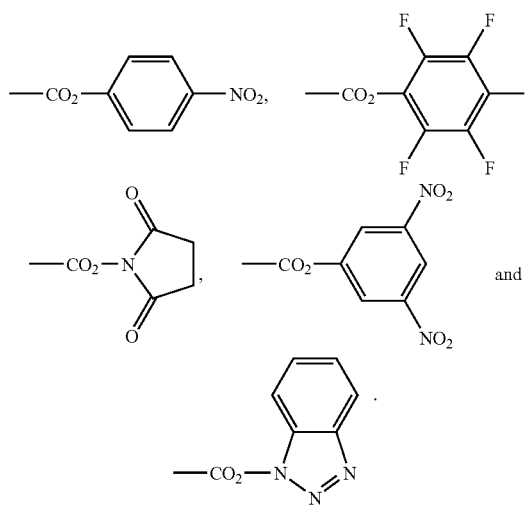

In formula I, Z stands for a hydrogen atom or a metal ion equivalent. Which metal ion in the compound according to the invention is to be complexed here depends on the intended use of the conjugates that are produced with the inventions according to the invention with a biomolecule. Corresponding conjugates are suitable, for example, for NMR diagnosis, radiodiagnosis and radiotherapy and neutron capture therapy. The conjugates in NMR diagnosis are especially preferably used as contrast media.

The production of complexes for NMR diagnosis can be carried out as was disclosed in Patents EP 71564, EP 130934 and DE-OS 34 01 052. To this end, the metal oxide or a metal salt (for example a chloride, nitrate, acetate, carbonate or sulfate) of the desired element is dissolved or suspended in water and/or a lower alcohol (such as methanol, ethanol or isopropanol) and reacted with the solution or suspension of the equivalent amount of the complexing agent according to the invention.

If the complexing agents are to be used for the production of radiodiagnostic agents or radiotherapeutic agents, the production of the complexes from the complexing agents can be carried out according to the methods that are described in "Radiotracers for Medical Applications," Vol. I, CRC Press, Boca Raton, Fla.

The compounds according to the invention are used
1. For NMR diagnosis in the form of their complexes with the ions of the paramagnetic elements with atomic numbers 21–29, 42, 44 and 58–70. Suitable ions are, for example, the chromium(III), ion(II), cobalt(II), nickel(II), copper(II), praseodymium(III), neodymium (III), samarium(III) and ytterbium(III) ion. Because of their strong magnetic moment, the gadolinum(II), terbium(III), dysprosium(III), holmium(III), erbium(III), manganese (II) and iron(III) ions are especially preferred for NMR diagnosis.
2. For radiodiagnosis and radiotherapy in the form of their complexes with the radioisotopes of elements with atomic numbers 26, 27, 29, 31, 32, 37–39, 43, 46, 47, 49, 61,62, 64, 67, 70, 71, 75, 77, 82 and 83.

The compounds according to the invention and especially their conjugates with biomolecules meet the many different requirements for suitability as contrast media for nuclear spin tomography. After oral or parenteral administration, they are thus extremely well suited for enhancing the informational value of the image that is obtained with the aid of a nuclear spin tomograph by increasing the signal intensity. They also show the high effectiveness that is necessary to load the body with the smallest possible amounts of foreign substances and the good compatibility that is necessary to maintain the non-invasive nature of the studies.

The good water solubility and low osmolality of the compounds according to the invention and their conjugates with biomolecules allow for the production of highly concentrated solutions so as to keep the volume burden of the circulatory system within reasonable limits and to offset the dilution by bodily fluids, i.e., NMR diagnostic agents have to be 100 to 1000 times more water-soluble than for NMR spectroscopy. In addition, the compounds according to the invention have not only a high stability in vitro but also a surprisingly high stability in vivo, so that a release or an exchange of the ions, which are inherently toxic and not covalently bonded in the complexes, is carried out only extremely slowly within the time that it takes for the new contrast media to be completely excreted again.

The complex compounds according to the invention can also be used advantageously as susceptibility reagents and as shift reagents for in vivo NMR spectroscopy.

The compounds according to the invention and their conjugates with biomolecules are also suitable as radiodiagnostic agents and radiotherapeutic agents based on their advantageous radioactive properties and the good stability of the complex compounds that are contained therein. Details of their use and dosage are described in, e.g., "Radiotracers for Medical Applications," CRC Press, Boca Raton, Fla. 1983, as well as in Eur. J. Nucl. Med. 17 (1990) 346–364 and Chem. Rev. 93 (1993) 1137–1156.

For SPECT, the complexes with isotopes $^{111}$In and $^{99m}$Tc are suitable.

Another imaging method with radioisotopes is the positron-emission tomography, which uses positron-emitting isotopes such as, e.g., $^{43}$Sc, $^{44}$Sc, $^{52}$Fe, $^{55}$Co, $^{68}$Ga, $^{64}$Cu, $^{86}$Y and $^{94m}$Tc (Heiss, W. D.; Phelps, M. E.; Positron Emission Tomography of Brain, Springer Verlag Berlin, Heidelberg, N.Y. 1983).

The compounds according to the invention and their conjugates with biomolecules are also suitable, surprisingly enough, for differentiating malignant and benign tumors in areas without blood-brain barriers.

They are distinguished in that they are completely eliminated from the body and thus are well-tolerated.

Since the compounds according to the invention and especially their conjugates with biomolecules accumulate in malignant tumors (no diffusion in healthy tissue, but high permeability of tumor vessels), they can also support the radiation therapy of malignant tumors. The latter is distinguished from the corresponding diagnosis only by the amount and type of the isotope that is used. The purpose in this case is the destruction of tumor cells by high-energy short-wave radiation with the lowest possible range of action. For this purpose, interactions of the metals that are contained in the complexes (such as, e.g., iron or gadolinium) with ionizing radiations (e.g., x rays) or with neutron rays are employed. By this effect, the local radiation dose at the site where the metal complex is found (e.g., in tumors) increases significantly. To produce the same radiation dose in the malignant tissue, radiation exposure for healthy tissue can be considerably reduced and thus burdensome side effects for the patients can be avoided when such metal complexes are used. The metal complex conjugates according to the invention are therefore also suitable as radiosensitizing substances in the radiation therapy of malignant tumors (e.g., exploiting Mössbauer effects or neutron capture therapy). Suitable β-emitting ions are, e.g., $^{46}$Sc, $^{47}$Sc, $^{48}$Sc, $^{72}$Ga, $^{73}$Ga, $^{90}$Y, $^{67}$Cu, $^{109}$Pd, $^{111}$Ag, $^{149}$Pm, $^{153}$Sm, $^{166}$Ho, $^{177}$Lu, $^{186}$Re and $^{188}$Re. $^{90}$Y, $^{177}$Lu, $^{72}$Ga, $^{153}$Sm and $^{67}$Cu are preferred. Suitable α-emitting ions that have short half-lives are, e.g., $^{211}$At, $^{211}$Bi, $^{212}$Bi, $^{213}$Bi and $^{214}$Bi, whereby $^{212}$Bi is preferred. A suitable photon- and electron-emitting ion is $^{158}$Gd, which can be obtained from $^{157}$Gd by neutron capture.

If the compound according to the invention or conjugate thereof with a biomolecule is intended for use in the variant of the radiation therapy that is proposed by R. L. Mills et al. [Nature Vol. 336 (1988), p. 787], the central ion must be derived from a Mössbauer isotope, such as, for example, $^{57}$Fe or $^{151}$Eu.

The neutralization of optionally still present free carboxy groups is carried out with the aid of inorganic bases (e.g., hydroxides, carbonates or bicarbonates) of, e.g., sodium, potassium, lithium, magnesium or calcium and/or organic bases, such as, i.a., primary, secondary and tertiary amines, such as, e.g., ethanolamine, morpholine, glucamine, N-methylglucamine and N,N-dimethylglucarnine, as well as basic amino acids, such as, e.g., lysine, arginine and ornithine or amides of originally neutral or acidic amino acids.

For the production of natural complex compounds, as much of the desired base can be added, for example, into acid complex salts in aqueous solution or suspension so that the neutral point is reached. The solution that is obtained can then be evaporated to the dry state in a vacuum. It is often advantageous to precipitate the neutral salts that are formed by adding water-miscible solvents, such as, e.g., lower alcohols (methanol, ethanol, isopropanol, etc.), lower ketones (acetone, etc.), polar ethers (tetrahydrofuran, dioxane, 1,2-dimethoyethane, etc.) and thus to obtain easily isolated and readily purified crystallizates. It has proven especially advantageous to add the desired base as early as during the complexing of the reaction mixture and thus to save a process step.

The compounds of formula I according to the invention can be produced according to the process that is known to one skilled in the art. For example, the compounds of formula I can be obtained by a process in which a compound of formula II

II in which B is defined as above is optionally reacted after introducing protective groups for the nitrogen atoms with Nu—A—X' and Nu—CH(R)—CO$_2$Z', whereby A and R are defined as above and Nu is a nucleofuge, X' stands for X or a protected form of X, and X is defined as above and Z' stands for a hydrogen atom, a metal ion equivalent, preferably an alkali metal or alkaline-earth metal, such as especially sodium or potassium, or a protective group for carboxyl. Then, the optionally present protective groups can be removed, and it can be reacted in a way that is known in the art with at least one metal oxide or metal salt of a desired element. Then, in the thus obtained complexes, still present acid hydrogen atoms optionally can be substituted completely or partially by cations of inorganic and/or organic bases, amino acids or amino acid amides.

Three preferred process variants are described in more detail below:

In the first variant, the macrocyclic compound that is unsubstituted at the nitrogens is first reacted with protected unit AX'. In this case, group A carries a nucleofuge as a leaving group. By stoichiometric reaction control, one of the four nitrogen atoms in the macrocyclic compound reacts with group A with the leaving group departing. In this way, a monofunctionalized macrocyclic compound that contains radical X in protected form (X') is obtained. In the second reaction step, the remaining three nucleophilic nitrogen atoms of the macrocyclic compound are reacted in each case with a protected carboxylic acid, which carries a nucleofuge in α-position in the carboxyl group. After the protective groups are cleaved off from the carboxylic acid functionalities, the complex that consists of paramagnetic metal ions and chelate ligands is finished by adding metal oxide or metal salt. This process variant is diagrammatically reproduced below, whereby the radicals in the formulas are defined as above:

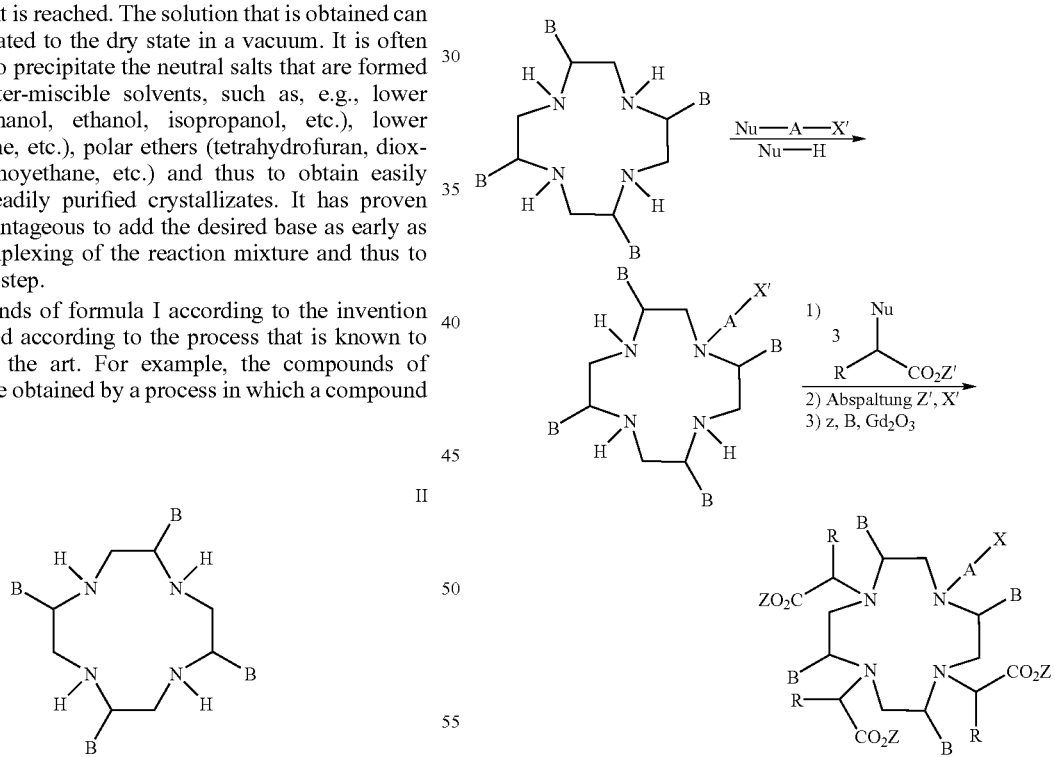

[Key:]
2) Cleavage Z', X'
3) e.g., Gd$_2$O$_3$
Nu=Nucleofuge (e.g., Br, I, O-triflate, mesylate, tosylate, etc.)
Z'=Protective group of the carboxylic acid In a second variant, a macrocyclic compound is used as an educt, which carries already suitable protective groups SG on three of the four nitrogen atoms. As protective groups, e.g., tert-butyl-oxycarbonyl (t-BOC), COCF$_3$, carbobenzoxy (Cbo) or fluorenyl-methoxycarbonyl (FMOC), etc. are suitable here. By the presence of the protective groups, only one of the four nitrogen atoms is nucleophilic and can react with A—X', which for its part carries a nucleofuge Nu as in the variant above. After linkage of both molecules with the leaving group departing, a cleavage of the three protective groups from the nitrogen atoms is carried out. It follows the derivatization with the aid of the carboxylic acid derivatives, as was already described for the variants above. This second process variant is diagrammatically reproduced below, whereby the radicals in the formulas are defined as above:

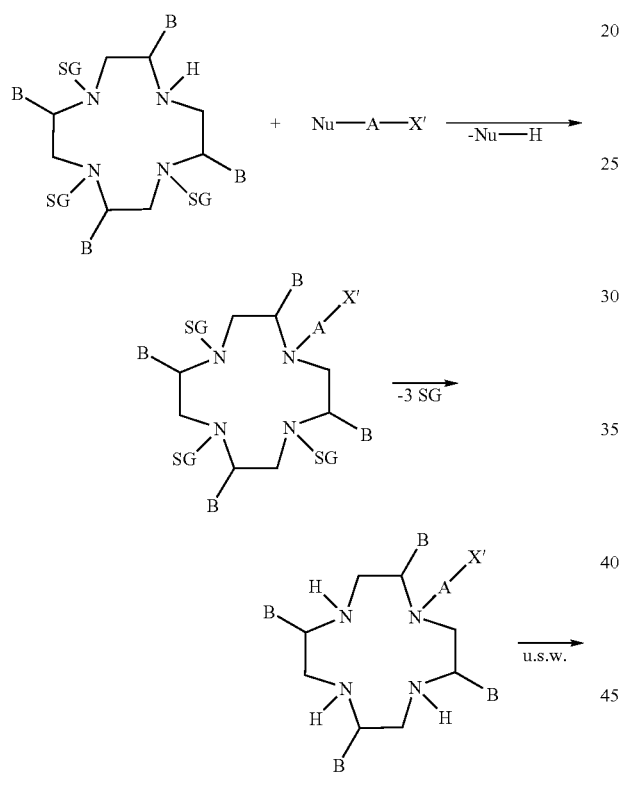

SG=Protective group (e.g., BOC, Cbo, COCF$_3$, FMOC, etc.)

In the third variant, first one of the four nitrogen atoms of the macrocyclic compound is blocked by a corresponding protective group SG. Examples of suitable protective groups are formyl, benzyl, boctrityl, etc. The reaction now is carried out on the three remaining nucleophilic nitrogen atoms with correspondingly protected carboxylic acid derivatives, which carry a corresponding nucleofuge in α-position. Then, the cleavage of protective group SG that is first introduced at the first nitrogen atom and derivatizing with AX', which for its part also carries a nucleofuge, are carried out. This third process variant is diagrammatically reproduced below, whereby the radicals in the formulas are defined as above:

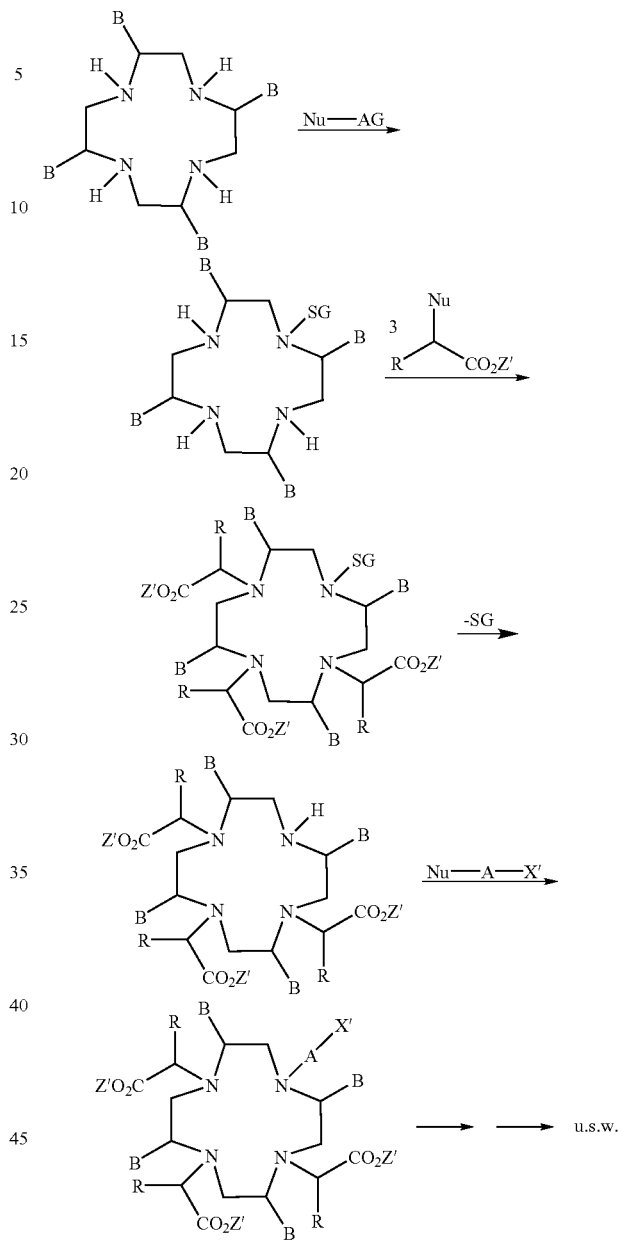

Advantageously used as a nucleofuge are the radicals: Cl, Br, I, O-triflate, mesylate and tosylate.

The reaction is performed in a mixture of water and organic solvents, such as: isopropanol, ethanol, methanol, butanol, dioxane, tetrahydrofuran, dimethylformamide, dimethyl acetamide, formamide or dichloromethane. Ternary mixtures that consist of water, isopropanol and dichloromethane are preferred.

The reaction is carried out in a temperature range of between −10° C. and 100° C., preferably between 0° C. and 30° C.

The protection of the above-named groups can be accomplished in numerous ways that are familiar to one skilled in the art. The embodiments that are described below are used to explain these protective group techniques without being limited to these synthesis methods.

As acid protective groups, $C_1$–$C_6$-alkyl, $C_6$–$C_{10}$-aryl and $C_6$–$C_{10}$—Ar($C_1$–$C_4$)-alkyl groups as well as trialkylsilyl groups are suitable. The methyl, ethyl, propyl, isopropyl, n-butyl, i-butyl and tert-butyl groups are preferred.

The cleavage of these acid protective groups is carried out according to the processes that are known to one skilled in the art, for example by hydrolysis, hydrogenolysis, alkaline saponification of the esters with alkali in aqueous-alcoholic solution at temperatures from 0 to 50° C., acidic saponification with mineral acids or in the case of tert-butyl esters with the aid of trifluoroacetic acid.

The NH groups can be protected in a variety of ways and then exposed again. The N-trifluoroacetyl derivative is cleaved by potassium or sodium carbonate in water (H. Newman, J. Org. Chem., 30: 287 (1965), M. A. Schwartz et al., J. Am. Chem. Soc., 95 G12 (1973)) or simply by ammonia solution (M. Imazama and F. Eckstein, J. Org. Chem., 44: 2039 (1979)). The tert-butyloxycarbonyl derivative is equally easy to cleave: stirring with trifluoroacetic acid suffices (B. F. Lundt et al., J. Org. Chem., 43: 2285 (1978)). The group of NH protective groups to be cleaved hydrogenolytically or in a reductive manner is very large: the N-benzyl group can be cleaved easily with hydrogen/Pd—C (W. H. Hartung and R. Rimonoff, Org. Reactions VII, 262 (1953)), which also applies for the trityl group (L. Zervas et al., J. Am. Chem. Soc., 78; 1359 (1956)) and the benzyloxycarbonyl group (M. Bergmann and L. Zervas Ber. 65: 1192 (1932)).

The activated esters of the above-described compounds are produced as known to one skilled in the art. For the case of isothiocyanates or α-haloacetates, the corresponding terminal amino precursors are reacted according to methods that are known in the literature with thiophosgene or 2-haloacetic acid-halides. The reaction with correspondingly derivatized esters of N-hydroxysuccinimide, such as, for example:

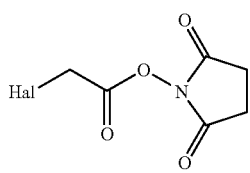

is also possible (Hal=halogen).

In general, for this purpose, all commonly used activation methods for carboxylic acids that are known in the prior art can be used. The molecule Nu—A—X is preferably synthesized first independently. If the molecule contains an amide group, the latter is produced, for example, by an activated carboxylic acid being reacted with an amine. The activation of the carboxylic acid is carried out according to the commonly used methods. Examples of suitable activating reagents are dicyclohexylcarbodiimide (DCC), 1-ethyl-3-(3-dimethylaminopropyl)-carbodiimide-hydrochloride (EDC), benzotriazol-1-yloxytris-(dimethylamino)-phosphonium hexafluorophosphate (BOP) and O-(benzotriazol-1-yl)-1,1,3,3-tetramethyluroniumhexafluorophosphate (HBTU), preferably DCC. The addition of O-nucleophilic catalysts, such as, e.g., N-hydroxysuccinimide (NHS) or N-hydroxybenzotriazole, is also possible.

If group X is a carboxylic acid function, the latter can be used in protected form (e.g., in the form of benzyl ester), and the cleavage of the protective group can then be carried out hydrogenolytically.

To link this carboxylic acid function to a suitable functional group of a suitable biomolecule, the latter should normally first be activated. Esters that are activated to this end are preferably produced at an intermediate stage, and said esters are then attacked by a nucleophilic group of the biomolecule. In this way, a covalent linkage between the biomolecule and the compound of formula I according to the invention is produced. Preferred activated esters are the esters of the N-hydroxysuccinimide, the esters of paranitrophenol or the esters of pentafluorophenol. If group X in the form of an isothiocyanate is linked to the biomolecule, a terminal amine is preferably first used which, if necessary, can be provided with a suitable protective group. Suitable protective groups are known from peptide chemistry. After the protective group is cleaved off, the isothiocyanate can be produced by reaction of the primary terminal amine with thiophosgene. Nucleophilic groups of the biomolecule can be added to the latter.

In an embodiment, group X represents a maleinimide, which can react, e.g., selectively with thiol functions of the biomolecule.

In another embodiment, group X is a nucleophile ($NH_2$, SH), which affects a suitable functionality of the biomolecule (activated ester, maleinimide, etc.). Numerous biomolecules that are functionalized with maleinimides are commercially available.

This invention, moreover, relates to the use of the above-described compounds of formula I for the production of conjugates with a biomolecule.

The synthesis of the conjugates is generally carried out in such a way that first a derivatized and functionalized chelate complex is produced that then is linked to the biomolecule. It is also possible, however, that if synthetically produced biomolecules are used, the chelate complex according to the invention is incorporated in the latter during the synthesis of the biomolecule. This can be carried out, for example, during the sequential synthesis of oligopeptides in the synthesizing robot. If necessary, the protective groups that are commonly used in the synthesis of the corresponding biomolecule can be introduced into the compound according to the invention. The latter are then cleaved again in the synthesizer in line with the usual synthesis algorithm.

"Biomolecule" is defined here as any molecule that either occurred naturally, for example in the body, or was produced synthetically with an analogous structure. Moreover, among the latter, those molecules are defined that can occur in interaction with a biological molecule that occurs, for example, in the body or a structure that occurs there, in such a way, for example, that the conjugates accumulate at specific desired spots of the body. "Body" is defined here as any plant or animal body, whereby animal and especially human bodies are preferred.

Biomolecules are especially the molecules that occur in living creatures that as products of an evolutionary selection by orderly and complex interactions meet specific objects of the organism and constitute the basis of its vital functions (changes in material and shape, reproduction, energy balance). In biomolecules, simple building blocks (amino acids, nucleobases, monosaccharides, fatty acids, etc.) of large molecules (proteins, nucleic acids, polysaccharides, lipids, etc.) are used in most cases. Corresponding macromolecules are also referred to as biopolymers.

The biomolecule advantageously can have, for example, a polypeptide skeleton that consists of amino acids with side chains that can participate in a reaction with reactive group X of the compounds of formula I according to the invention. Such side chains include, for example, the carboxyl groups of aspartic acid and glutamic acid esters, the amino groups of lysine radicals, the aromatic groups of tyrosine and histidine radicals and the sulfhydryl groups of cysteine radicals.

A survey on biomolecules with numerous examples is found in the manuscript "Chemie der Biomoleküle [Chemistry of Biomolecules]" of TU-Graz (H. Berthold et al., Institut fir Organische Chemie [Institute for Organic Chemistry], Tu-Graz, 2001), which can also be seen on the Internet under www.orgc.tu-graz.ac.at. The content of this document is integrated by reference in this description.

To form conjugates with the compounds according to the invention, the following biomolecules are especially suitable:

Biopolymers, proteins, such as proteins that have a biological function, HSA, BSA, etc., proteins and peptides, which accumulate at certain spots in the organism (e.g., in receptors, cell membranes, at ducts, etc.), peptides that can be cleaved by proteases, peptides with predetermined synthetic sites of rupture (e.g., labile esters, amides, etc.), peptides that are cleaved by metalloproteases, peptides with photocleavable linkers, peptides with oxidative agents (oxydases) and cleavable groups, peptides with natural and unnatural amino acids, glycoproteins (glycopeptides), signal proteins, antiviral proteins and apoctosis, synthetically modified biopolymers such as biopolymers that are derivatized with linkers, modified metalloproteases and derivatized oxydase, etc., carbohydrates (mono- to polysaccharides), such as derivatized sugars, sugars that can be cleaved in the organism, cyclodextrins and derivatives thereof, amino sugars, chitosan, polysulfates and acetylneuraminic acid derivatives, antibodies, such as monoclonal antibodies, antibody fragments, polyclonal antibodies, minibodies, single chains (also those that are linked by linkers to multiple fragments), red blood corpuscles and other blood components, cancer markers (e.g., CAA) and cell adhesion substances (e.g., Lewis X and anti-Lewis X derivatives), DNA and RNA fragments, such as derivatized DNAs and RNAs (e.g., those that were found by the SELEX process), synthetic RNA and DNA (also with unnatural bases), PNAs (Hoechst) and antisense, β-amino acids (Seebach), vector amines for transfer into the cell, biogenic amines, pharmaceutical agents, oncological preparations, synthetic polymers, which are directed to a biological target (e.g., receptor), steroids (natural and modified), prostaglandins, taxol and derivatives thereof, endothelins, alkaloids, folic acid and derivatives thereof, bioactive lipids, fats, fatty acid esters, synthetically modified mono-, di- and triglycerides, liposomes, which are derivatized on the surface, micelles that consist of natural fatty acids or perfluoroalkyl compounds, porphyrins, texaphrines, expanded porphyrins, cytochromes, inhibitors, neuramidases, neuropeptides, immunomodulators, such as FK 506, CAPE and gliotoxin, endoglycosidases, substrates that are activated by enzymes such as calmodulin kinase, casein-kinase II, glutathione-S-transferase, heparinase, matrix-metalloproteases, β-insulin-receptor-kinase, UDP-galactose 4-epimerase, fucosidases, G-proteins, galactosidases, glycosidases, glycosyltransferases and xylosidase, antibiotics, vitamins and vitamin analogs, hormones, DNA intercalators, nucleosides, nucleotides, lectins, vitamin B12, Lewis-X and related substances, psoralens, dienetriene antibiotics, carbacyclins, VEGF (vascular endothelial growth factor), somatostatin and derivatives thereof, biotin derivatives, antihormones, tumor-specific proteins and synthetic agents, polymers that accumulate in acidic or basic areas of the body (pH-controlled dispersion), myoglobins, apomyoglobins, etc., neurotransmitter peptides, tumor necrosis factors, peptides that accumulate in inflamed tissues, blood-pool reagents, anion and cation-transporter proteins, polyesters (e.g., lactic acid), polyamides and polyphosphates.

Most of the above-mentioned biomolecules are commercially available from, for example, Merck, Aldrich, Sigma, Calibochem or Bachem.

In addition, all "plasma protein binding groups" or "target binding groups" that are disclosed in WO 96/23526 and WO 01/08712 can be used as biomolecules. The content of these two laid-open specifications is therefore integrated by reference into this description.

The number of compounds of formula I according to the invention per biomolecule is random in principle, but a molecular ratio of 0.1:1 to 10:1, especially 0.5:1 to 7:1, is preferred.

The compounds according to the invention are also suitable for conjugation on all molecules that are reacted with fluorescence dyes in the prior art to determine, for example, their location by epifluorescence microscopy within the cell. After the administration of the medication, the compounds with, in principle, any medications can also be conjugated to then track the transport within the organism, for example by the NMR technique. It is also possible that the conjugates from the compounds according to the invention and the biomolecules contain other additional molecules, which had been conjugated on the biomolecules. The term "biomolecule" in terms of this invention thus encompasses all molecules that occur in the biological systems and all molecules that are biocompatible.

The conjugates that are obtained with the compounds according to the invention are preferably used as contrast media in NMR diagnosis. The conjugates should therefore be water-soluble. If the conjugates that are obtained with the compounds according to the invention are to be used as NMR contrast media, they are preferably dosed in an amount of 0.0001–5 mmol/kg of body weight and especially preferably in an amount of 0.005–0.5 mmol/kg of body weight. Details of use are discussed in, e.g., H.-J. Weinmann et al., Am. J. of Roentgenology 142, 619 (1984). By the surprisingly high relaxivity of the compounds according to the invention with simultaneous target specificity of the conjugates that are obtained with these compounds, the latter can be especially low-dosed, for example, to detect tumors.

Details of use of radiotherapeutic agents are discussed in, e.g., R. W. Kozak et al. TIBTEC, October 1986, 262 (see above Bioconjugate Chem. 12 (2001) 7–34).

This invention is explained in more detail by the examples below without being limited thereto.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE

Example 1 a) 10-[4-(Benzyloxycarbonyl)-1-methyl-2-oxo-3-azabutyl]-1,4,7-α,α',α"-trimethyl-1,4,7-tris-(benzyloxycarbonylmethyl)-1,4,7,10-tetraazacyclododecane 25 g (81.1 mmol) of 2-bromopropionylglycine-benzyl ester (Example 1e of WO 98/24774) is added to 27.9 g (162.2 mol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: chloroform/methanol/aqueous 25% ammonia=10/5/1). The thus obtained 1-[4-(benzyloxycarbonyl)-1-methyl-2-oxo-3-azabutyl]-1,4,7,10-tetraazacyclododecane (19.6 g; 50 mmol; 62% of theory) and 60 ml (0.35 mol) of N-ethyldiisopropylamine in 200 ml of dichloromethane are added to 62.45 g (0.2 mol) of 2-(trifluoromethanesulfonyloxy)-propanoic acid benzyl ester (Kitazaki et al., Chem. Pharm. Bull. (1999), 47(3), 360) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 32.0 g (73% of theory) of a colorless, crystalline powder Elementary analysis: Cld.: C, 68.39; H, 7.23; N, 7.98. Fnd.: C, 67.95; H, 7.41; N, 8.22.

b) 10-(4-Carboxy-1-methyl-2-oxo-3-azabutyl)-1,4,7α,α',α"-trimethyl-1,4,7-tris(carboxy-methyl)-1,4,7,10-tetraazacyclododecane 26.3 g (30 mmol) of the title compound of Example 1a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 15.7 g (quantitative) of a colorless powder Elementary analysis: Cld.: C, 51.05; H, 7.60; N, 13.53. Fnd.: C, 50.71; H, 7.83; N, 13.25.

c) Gd Complex of 10-(4-carboxy-1-methyl-2-oxo-3-azabutyl)-1,4,7-α,α',α"-trimethyl-1,4,7-tris(carboxymethyl)-1,4,7,10-tetraazacyclododecane 10.4 g (20 mmol) of the ligand that is described in Example 1b is dissolved in 200 ml of water and 80 ml of isopropanol, and it is acidified by adding 5 ml of acetic acid. 3.6 g (10 mmol) of gadolinium oxide is added, and it is refluxed for 3 hours. After complexing is completed, it is set at pH 7.4 again with ammonia and chromatographed on silica gel (mobile solvent: dichloromethane/methanol/ammonia: 20/20:1). The fractions that contain the product are combined and added via an IR-120® cation exchange column (H⁺ form). The acidic eluate is freeze-dried.

Yield: 10.1 g (69% of theory) of a colorless powder. Water content (Karl-Fischer): 8.3% Elementary analysis (relative to anhydrous substance): Cld.: C, 39.33; H, 5.40; Gd, 23.41 N, 10.42. Fnd.: C, 39.21; H, 5.88; Gd, 22.93; N; 10.11.

Example 2 a) 10-[4-(Benzyloxycarbonyl)-1-methyl-2-oxo-3-azabutyl]-1,4,7-α,α',α"-tris(isopropyl)-1,4,7-tris(benzyloxycarbonylmethyl)-1,4,7,10-tetraazacyclododecane 19.6 g (50 mmol) of the 1-[4-(benzyloxy-carbonyl)-1-methyl-2-oxo-3-azabutyl]-1,4,7,10-tetraazacyclododecane that is described in Example 1a as an intermediate product and 60 ml (0.35 mol) of N-ethyldiisopropylamine in 200 ml of dichloromethane are added to 68.1 g (0.2 mol) of 2-(trifluoromethanesulfonyloxy)-isovaleric acid benzyl ester (Walker et al., Tetrahedron (1997), 53(43), 14591) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 33.7 g (70% of theory) of a colorless, crystalline powder Elementary analysis: Cld.: C, 69.90; H, 7.86; N, 7.28. Fnd.: C, 69.77; H, 17.51; N, 7.22.

b) 10-(4-Carboxy-1-methyl-2-oxo-3-azabutyl)-1,4,7-α,α',α"-tris(isopropyl)-1,4,7-tris(carboxymethyl)-1,4,7,10-tetraazacyclododecane 28.9 g (30 mmol) of the title compound of Example 2a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 18.0 g (quantitative) of a colorless powder Elementary analysis: Cld.: C, 55.89; H, 8.54; N, 11.64. Fnd.: C, 55.63; H, 8.83; N, 11.31.

c) Gd Complex of 10-(4-carboxy-1-methyl-2-oxo-3-azabutyl)-1,4,7-α,α',α"-tris(isopropyl)-1,4,7-tris(carboxymethyl)-1,4,7,10-tetraazacyclododecane 12.0 g (20 mmol) of the ligand that is described in Example 2b is dissolved in 200 ml of water and 80 ml of isopropanol and acidified by adding 5 ml of acetic acid. 3.6 g (10 mmol) of gadolinium oxide is added, and it is refluxed for 3 hours. After complexing is completed, it is set at pH 7.4 with ammonia and chromatographed on silica gel (mobile solvent: dichloromethane/methanol/ammonia: 20/20/1). The fractions that contain the product are combined and added via an IR-120® cation exchange column (H⁺ form). The acidic eluate is freeze-dried.

Yield: 12.0 g (72% of theory) of a colorless powder. Water content (Karl-Fischer): 9.1% Elementary analysis (relative to anhydrous substance): Cld.: C, 44.49; H, 6.40; Gd, 20.80; N, 9.26. Fnd.: C, 44.21; H, 6.72; Gd, 20.23; N, 9.11.

Example 3 a) 10-[4-(Benzyloxycarbonyl)-1-methyl-2-oxo-3-azabutyl]-1,4,7-α,α',α"-tris(cyclohexyl)-1,4,7-tris(benzyloxycarbonylmethyl)-1,4,7,10-tetraazacyclododecane 19.6 g (50 mmol) of 1-[4-(benzyloxy-carbonyl)-1-methyl-2-oxo-3-azabutyl]-1,4,7,10-tetraazacyclododecane that is described in Example 1a as an intermediate product and 60 ml (0.35 mol) of N-ethyldiisopropylamine in 200 ml of dichloromethane are added to 76.1 g (0.2 mol) of 2-(trifluoromethanesulfonyloxy)-2-cyclohexylacetic acid benzyl ester (Qabar et al., Tetrahedron Letters (1998), 39(33), 5895) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 41.1 g (76% of theory) of a colorless, crystalline powder Elementary analysis: Cld.: C, 72.13; H, 8.10; N, 6.47. Fnd.: C, 71.88; H, 8.21; N, 6.25.

b) 10-(4-Carboxy-1-methyl-2-oxo-3-azabutyl)-1,4,7-α,α',α''-tris(cyclohexyl)-1,4,7-tris(carboxymethyl)-1,4,7,10-tetraazacyclododecane 32.5 g (30 mmol) of the title compound of Example 3a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 22.0 g (quantitative) of a colorless powder Elementary analysis: Cld.: C, 61.56; H, 8.80; N, 9.70. Fnd.: C, 61.17; H, 8.98; N, 9.41.

c) Gd Complex of the 10-(4-carboxy-1-methyl-2-oxo-3-azabutyl)-1,4,7-α,α',α''-tris(cyclohexyl)-1,4,7-tris(carboxymethyl)-1,4,7,10-tetraazacyclododecane 14.4 g (20 mmol) of the ligand that is described in Example 3b is dissolved in 150 ml of water and 150 ml of isopropanol and acidified by adding 5 ml of acetic acid. 3.6 g (10 mmol) of gadolinium oxide is added, and it is refluxed for 8 hours. After complexing is completed, it is set at pH 7.4 again with ammonia and chromatographed on silica gel (mobile solvent: dichloromethane/methanol/ammonia: 20/20/1). The fractions that contain the product are combined and evaporated to the dry state. The residue is taken up with formic acid and evaporated to the dry state several times with the addition of dichloromethane and then dried in a vacuum until a constant weight is reached.

Yield: 12.4 g (65% of theory) of a colorless powder. Water content (Karl-Fischer): 8.0% Elementary analysis (relative to anhydrous substance): Cld.: C, 50.72; H, 6.90; Gd, 17.95; N, 7.99. Fnd.: C, 51.03; H, 7.08; Gd, 17.42; N, 8.11.

Example 4 a) 10-[4-(t-Butoxycarbonyl)-1-phenyl-2-oxo-3-azabutyl]-1,4,7-α,α',α''-trimethyl-1,4,7-tris-(benzyloxycarbonylmethyl)-1,4,7,10-tetraazacyclododecane 26.6 g (81.1 mmol) of N-[2-bromo-2-phenylacetyl]-glycine-t-butylester (Example 6a of WO 98/24775) is added to 27.9 g (162.2 mmol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: chloroform/methanol/aqueous 25% ammonia=10/5/1). The thus obtained 1-[4-(t-butoxycarbonyl)-1-phenyl-2-oxo-3-azabutyl]-1,4,7,10-tetraazacyclododecane (21.0 g; 50 mmol; 62% of theory) and 60 ml (0.35 mol) of N-ethyldiisopropylamine in 200 ml of dichloromethane are added to 62.45 g (0.2 mol) of 2-(trifluoromethanesulfonyl-oxy)propanoic acid benzyl ester (Kitazaki et al., Chem. Pharm. Bull. (1999), 47(3), 360) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 34.0 g (75% of theory) of a colorless, crystalline powder Elementary analysis: Cld.: C, 68.93; H, 7.45; N, 7.73. Fnd.: C, 69.12; H, 7.57; N, 7.60.

b) 10-(4-(t-Butyloxycarbonyl-1-phenyl-2-oxo-3-azabutyl)-1,4,7-α,α',α''-trimethyl-1,4,7-tris(carboxymethyl)-1,4,7,10-tetraazacyclododecane 27.2 g (30 mmol) of the title compound of Example 4a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 17.5 g (quantitative) of a colorless powder Elementary analysis: Cld.: C, 55.95; H, 7.13; N, 12.08. Fnd.: C, 56.21; H, 6.99; N, 11.83.

c) Gd Complex of 10-(4-carboxy-1-phenyl-2-oxo-3-azabutyl)-1,4,7-α,α',α''-trimethyl-1,4,7-tris(carboxymethyl)-1,4,7,10-tetraazacyclododecane 11.6 g (20 mmol) of the t-butylester that is described in Example 4b is dissolved in a very little trifluoroacetic acid and stirred for 15 minutes at room temperature. After 250 ml of diethyl ether is added, it is stirred for 2 more hours, the precipitate is suctioned off and dried in a vacuum. The thus obtained free ligand is dissolved in 200 ml of water and 80 ml of isopropanol, set at pH 7 with dilute ammonia and acidified by adding 5 ml of acetic acid. 3.6 g (10 mmol) of gadolinium oxide is added, and it is refluxed for 3 hours. After complexing is completed, it is set at pH 7.4 again with ammonia and chromatographed on silica gel (mobile solvent: dichloromethane/methanol/ammonia: 20/20/1). The fractions that contain the product are combined and added via an IR-120® cation exchange column (H⁺ form). The acidic eluate is freeze-dried.

Yield: 11.6 g (72% of theory) of a colorless powder. Water content (Karl-Fischer): 9.0% Elementary analysis (relative to anhydrous substance): Cld.: C, 44.19; H, 5.22; Gd, 21.43; N, 9.54. Fnd.: C, 43.91; H, 5.27; Gd, 21.09; N, 9.77.

Example 5 a) 4-(Ethoxycarbonylmethoxy)-phenylacetic acid methyl ester 10 g (60.2 mmol) of hydroxyphenylacetic acid methyl ester (Aldrich) is dissolved in 75 ml of acetone. 18.4 g (133 mmol) of solid potassium carbonate is added. 17.8 ml (123 mmol) of bromoacetic acid ethyl ester is added in drops under reflux within 15 minutes, it is kept at this temperature for another 4 hours, and it is stirred overnight at room temperature. Precipitate is filtered out, the solution is evaporated to the dry state and chromatographed on silica gel (hexane/ethyl acetate 3:1). The fractions that contain the product are combined and concentrated by evaporation.

Yield: 14.6 g (96% of theory) Elementary analysis: Cld.: C, 61.90; H, 6.39. Fnd.: C, 61.67; H, 6.50.

b) α-Bromo-4-(ethoxycarbonylmethoxy)-phenylacetic acid methyl ester 13.5 g (53.5 mmol) of the title compound of Example 5a is dissolved in 75 ml of carbon tetrachloride. 9.52 g (53.5 mmol) of N-bromosuccinimide and 48 mg of dibenzoyl peroxide are added, refluxed for 5 hours and stirred overnight at room temperature. The suspension is washed twice with sodium bicarbonate solution and once with water, the organic phase is dried with magnesium sulfate, desiccant is suctioned off, and the filtrate is evaporated to the dry state in a vacuum. The residue is chromatographed on silica gel (hexane/ethyl acetate 3:1). The fractions that contain the product are combined and concentrated by evaporation.

Yield: 15.4 g (87% of theory) Elementary analysis: Cld.: C, 47.15; H, 4.57; Br, 24.13. Fnd.: C, 47.01; H, 4.76; Br, 23.70.

c) 10-[α-(4-(Ethoxycarbonylmethoxy)phenyl)-methoxycarbonylmethyl]-1,4,7-α,α',α''-trimethyl-1,4,7-tris(benzyloxycarbonylmethyl)-1,4,7,10-tetraazacyclododecane 26.9 g (81.1 mmol) of the bromine compound that is described in Example 5b above is added to 27.9 g (162.2 mmol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: dichloromethane/methanol/triethylamine=10/5/0.1). The thus obtained 1-[α-(4-(ethoxy-carbonylmethoxy)phenyl)-methoxycarbonylmethyl]-1,4,7,10-tetraazacyclododecane (21.1 g; 50 mmol; 62% of theory) and 60 ml (0.35 mol) of N-ethyldiisopropylamine in 200 ml of dichloromethane are added to 62.45 g (0.2 mol) of 2-(trifluoromethanesulfonyloxy)propanoic acid benzyl ester (Kitazaki et al., Chem. Pharm. Bull. (1999), 47(3), 360) in 400 ml of dichloromethane; and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 34.1 g (75% of theory) of a colorless, crystalline powder Elementary analysis: Cld.: C, 67.38; H, 7.10; N, 6.16. Fnd.: C, 67.20; H, 7.33; N, 6.31.

d) 10-[α-(4-(Ethoxycarbonylmethoxy)phenyl)-methoxycarbonylmethyl]-1,4,7-α,α',α''-trimethyl-1,4,7-tris(carboxymethyl)-1,4,7,10-tetraazacyclododecane 27.3 g (30 mmol) of the title compound of Example 5c is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 19.3 g (quantitative) of a colorless powder Elementary analysis: Cld.: C, 56.42; H, 7.26; N, 8.77. Fnd.: C, 56.21; H, 7.56; N, 8.47.

e) Gd Complex of 10-[α-(4-carboxymethoxyphenyl)-carboxymethyl]-1,4,7-α,α',α''-trimethyl-1,4,7-tris(carboxymethyl)-1,4,7,10-tetraazacyclododecane 13.3 g (20 mmol) of the title compound of Example 5d is taken up in 250 ml of 2N sodium hydroxide solution and 250 ml of tetrahydrofuran, and it is stirred for 5 days at 40° C. Then, the aqueous phase is set at pH 7 with Amberlite IR-120® (H$^+$ form), 80 ml of isopropanol is added, and it is acidified by adding 5 ml of acetic acid. 3.6 g (10 mmol) of gadolinum oxide is added, and it is refluxed for 3 hours. After complexing is completed, it is set at pH 7.4 again with ammonia and chromatographed on silica gel (mobile solvent: dichloromethane/methanol/ammonia: 20/20/1). The fractions that contain the product are combined and added via an IR-120® cation exchange column (H$^+$ form). The acidic eluate is freeze-dried.

Yield: 8.6 g (61% of theory) of a colorless powder. Water content (Karl-Fischer): 9.3% Elementary analysis (relative to anhydrous substance): Cld.: C, 43.19; H, 4.97; Gd, 20.94; N, 7.46. Fnd.: C, 43.22; H, 5.29; Gd, 20.42; N, 7.11.

Example 6 a) 4-(Ethoxycarbonylpropoxy)-phenylacetic acid methyl ester 10 g (60.2 mmol) of hydroxyphenylacetic acid methyl ester (Aldrich) is dissolved in 75 ml of acetone. 18.4 g (133 mmol) of solid potassium carbonate is added. 17.8 ml (123 mmol) of 4-bromobutyric acid ethyl ester is added in drops under reflux within 15 minutes, and it is kept at this temperature for another 4 hours and stirred overnight at room temperature. Precipitate is filtered out, the solution is evaporated to the dry state, and it is chromatographed on silica gel (hexane/ethyl acetate 3:1). The fractions that contain the product are combined and concentrated by evaporation.

Yield: 16.4 g (97% of theory) Elementary analysis: Cld.: C, 64.27; H, 7.19. Fnd.: C, 64.41; H, 6.92.

b) α-Bromo-[4-(ethoxycarbonylpropoxy)-phenyl]-acetic acid methyl ester 15.0 g (53.5 mmol) of the title compound of Example 6a is dissolved in 75 ml of carbon tetrachloride. 9.52 g (53.5 mmol) of N-bromosuccinimide and 48 mg of dibenzoyl peroxide are added, and it is refluxed for 5 hours and stirred overnight at room temperature. The suspension is washed twice with sodium bicarbonate solution and once with water, the organic phase is dried with magnesium sulfate, desiccant is filtered out, and the filtrate is evaporated to the dry state in a vacuum. The residue is chromatographed on silica gel (hexane/ethyl acetate 3:1). The fractions that contain the product are combined and concentrated by evaporation.

Yield: 15.9 g (83% of theory) Elementary analysis: Cld.: C, 50.16; H, 5.33; Br, 22.24. Fnd.: C, 50.33; H, 5.04; Br, 21.94.

c) 10-[α-(4-(Ethoxycarbonylpropoxy)phenyl)-methoxycarbonylmethyl]-1,4,7-α,α',α''-trimethyl-1,4,7-tris(benzyloxycarbonylmethyl)-1,4,7,10-tetraazacyclododecane 29.1 g (81.1 mmol) of the bromine compound that is described in Example 6b above is added to 27.9 g (162.2 mmol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: dichloromethane/methanol/triethylamine=10/5/0.1). The thus obtained 1-[α-(4-(ethoxy-carbonylpropoxy)phenyl)methoxycarbonylmethyl]-1,4,7,10-tetraazacyclododecane (22.5 g; 50 mmol; 62% of theory) and 60 ml (0.35 mol) of N-ethyldiisopropylamine in 200 ml of dichloromethane are added to 62.45 g (0.2 mol) of 2-(trifluoromethanesulfonyloxy)-propanoic acid-benzyl ester (Kitazaki et al., Chem. Pharm. Bull. (1999), 47(3), 360) in 400 ml of dichloromethane, and it is refluxed for 6 hours and then overnight at room temperature. It is extracted three times with 500 ml each of water, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 30.5 g (65% of theory) of a colorless, crystalline powder Elementary analysis: Cld.: C, 67.93; H, 7.31; N, 5.98. Fnd.: C, 67.95; H, 7.22; N, 6.13.

d) 10-[α-(4-(Ethoxycarbonylpropoxy)phenyl)-methoxycarbonylmethyl]-1,4,7-α,α',α''-trimethyl-1,4,7-tris(carboxymethyl)-1,4,7,10-tetraazacyclododecane 28.1 g (30 mmol) of the title compound of Example 6c is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 20.0 g (quantitative) of a colorless powder Elementary analysis: Cld.: C, 57.64; H, 7.56; N, 8.40. Fnd.: C, 57.43; H, 7.77; N, 8.69.

e) Gd Complex of 10-[α-(4-carboxypropoxyphenyl)-carboxymethyl]-1,4,7-α,α',α''-trimethyl-1,4,7-tris(carboxymethyl)-1,4,7,10-tetraazacyclododecane 13.3 g (20 mmol) of the title compound of Example 6d is taken up in 250 ml of 2N sodium hydroxide solution and 250 ml of tetrahydrofuran, and it is stirred for 5 days at 40° C. Then, the aqueous phase is set at pH 7 with Amberlite IR-120® (H$^+$ form), 80 ml of isopropanol is added, and it is acidified by adding 5 ml of acetic acid. 3.6 g (10 mmol) of gadolinium oxide is added, and it is refluxed for 3 hours. After complexing is completed, it is set at pH 7.4 again with ammonia and chromatographed on silica gel (mobile solvent: dichloromethane/methanol/ammonia: 20/20/1). The fractions that contain the product are combined and added via an IR-120® cation exchange column (H$^+$ form). The acidic eluate is freeze-dried.

Yield: 9.3 g (55% of theory) of a colorless powder. Water content (Karl-Fischer): 8.0% Elementary analysis (relative to anhydrous substance): Cld.: C, 44.72; H, 5.31; Gd, 20.19; N, 7.19. Fnd.: C, 44.31; H, 5.88; Gd, 19.93; N, 7.11.

Example 7 a) 4-(Ethoxycarbonyldecyloxy)-phenylacetic acid methyl ester 10 g (60.2 mmol) of hydroxyphenylacetic acid methyl ester (Aldrich) is dissolved in 75 ml of acetone. 18.4 g (133 mmol) of solid potassium carbonate is added, 36.1 g (123 mmol) of ω-bromoundecanoic acid ethyl ester in 50 ml of acetone is added in drops, refluxed for 8 hours and stirred overnight at room-temperature. The undissolved material is filtered out, the solution is evaporated to the dry state and chromatographed on silica gel (hexane/ethyl acetate 3:1). The fractions that contain the product are combined and concentrated by evaporation.

Yield: 20.3 g (89% of theory) Elementary analysis: Cld.: C, 69.81; H, 9.05. Fnd.: C, 69.50; H, 8.91.

b) α-Bromo-[4-(ethoxycarbonyldecyloxy)-phenyl]-acetic acid methyl ester 20.2 g (53.5 mmol) of the title compound of Example 7a is dissolved in 75 ml of carbon tetrachloride. 9.52 g (53.5 mmol) of N-bromosuccinimide and 48 mg of dibenzoyl peroxide are added, refluxed for 5 hours and stirred overnight at room temperature. The suspension is washed twice with sodium bicarbonate solution and once with water, the organic phase is dried with magnesium sulfate, desiccant is filtered out, and the filtrate is evaporated to the dry state in a vacuum. The residue is chromatographed on silica gel (hexane/ethyl acetate 3:1). The fractions that contain the product are combined and concentrated by evaporation.

Yield: 21.0 g (86% of theory) Elementary analysis: Cld.: C, 57.77; H, 7.27; Br, 17.47. Fnd.: C, 57.95; H, 7.41; Br, 17.02.

c) 10-[α-(4-(Ethoxycarbonyldecyloxy)phenyl)-methoxycarbonylmethyl]-1,4,7-α,α',α''-trimethyl-1,4,7-tris(benzyloxycarbonylmethyl)-1,4,7,10-tetraazacyclododecane 37.1 g (81.1 mmol) of the bromine compound that is described in Example 7b above is added to 27.9 g (162.2 mmol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: dichloromethane/methanol/triethylamine=10/5/0.1). The thus obtained 1-[α-(4-(ethoxy-carbonyldecyloxy)phenyl)-methoxycarbonylmethyl]-1,4,7,10-tetraazacyclododecane (27.4 g; 50 mmol; 62% of theory) and 60 ml (0.35 mol) of N-ethyldiisopropylamine in 200 ml of dichloromethane are added to 62.45 g (0.2 mol) of 2-(trifluoromethanesulfonyloxy)propanoic acid benzyl ester (Kitazaki et al., Chem. Pharm. Bull. (1999), 47(3), 360) in 400 ml of dichloromethane, and it is stirred for 6 hours under reflux and then overnight at room temperature. It is extracted three times with 500 ml of water each, the organic phase is dried on magnesium sulfate, and it is evaporated to the dry state. The residue is chromatographed on silica gel (mobile solvent: dichloromethane/methanol: 20/1). The fractions that contain the product are combined and concentrated by evaporation.

Yield: 33.6 g (65% of theory) of a colorless, crystalline powder Elementary analysis: Cld.: C, 69.61; H, 7.98; N, 5.41. Fnd.: C, 69.75; H, 7.88; N, 5.12.

d) 10-[α-(4-(Ethoxycarbonyldecyloxy)phenyl)-methoxycarbonylmethyl]-1,4,7-α,α',α"-trimethyl-1,4,7-tris(carboxymethyl)-1,4,7,10-tetraazacyclododecane 31.1 g (30 mmol) of the title compound of Example 7c is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 23.0 g (quantitative) of a colorless powder Elementary analysis: Cld.: C, 61.24; H, 8.43; N, 7.32. Fnd.: C, 60.96; H, 8.61; N, 7.22.

e) Gd Complex of 10-[α-(4-carboxydecyloxyphenyl)-carboxymethyl]-1,4,7-α,α',α"-trimethyl-1,4,7-tris(carboxymethyl)-1,4,7,10-tetraazacyclododecane 15.3 g (20 mmol) of the title compound of Example 7d is taken up in 250 ml of 2N sodium hydroxide solution and 250 ml of tetrahydrofuran, and it is stirred for 5 days at 40° C. Then, the aqueous phase is set at pH 7 with Amberlite IR-120® (H+ form), 80 ml of isopropanol is added, and it is acidified by adding 5 ml of acetic acid. 3.6 g (10 mmol) of gadolinium oxide is added, and it is refluxed for 3 hours. After complexing is completed, it is set at pH 7.4 again with ammonia, and it is chromatographed on silica gel (mobile solvent: dichloromethane/methanol/ammonia: 20/20/1). The fractions that contain the product are combined and added via an IR-120® cation exchange column (H+ form). The acidic eluate is freeze-dried.

Yield: 11.5 g (60% of theory) of a colorless powder. Water content (Karl-Fischer): 8.5% Elementary analysis (relative to anhydrous substance): Cld.: C, 49.30; H, 6.32; Gd, 17.93; N, 6.39. Fnd.: C, 49.56; H, 6.10; Gd, 17.52; N, 6.63.

Example 8 a) 10-(p-Methoxycarbonylbenzyl)-1,4,7-α,α',α"-trimethyl-1,4,7-tris(benzyloxycarbonyl-methyl)-1,4,7,10-tetraazacyclododecane 18.6 g (81.1 mmol) of 4-bromomethyl-benzoic acid methyl ester (Aldrich) in 150 ml of chloroform is added to 27.9 g (162.2 mmol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: methanol/aqueous 25% ammonia=8/1). The thus obtained 1-(p-methoxycarbonylbenzyl)-1,4,7,10-tetraazacyclododecane (21.6 g; 67.3 mmol; 83% of theory) and 60 ml (0.35 mol) of N-ethyldiisopropylamine in 200 ml of dichloromethane are added to 62.45 g (0.2 mol) of 2-(trifluoromethanesulfonyloxy)propanoic acid benzyl ester (Kitazaki et al., Chem. Pharm. Bull. (1999), 47(3), 360) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 41.8 g (77% of theory) of a colorless, crystalline powder Elementary analysis: Cld.: C, 69.95; H, 7.24; N, 6.94. Fnd.: C, 69.57; H, 7.39; N, 7.12.

b) 10-(p-Carboxybenzyl)-1,4,7-α,α',α"-trimethyl-1,4,7-tris(carboxymethyl)-1,4,7,10-tetraazacyclododecane 24.2 g (30 mmol) of the title compound of Example 8a is dissolved in 400 ml of methanol, mixed with 100 ml of 15N sodium hydroxide solution, refluxed for 6 hours and stirred overnight at room temperature. After concentration by evaporation in a vacuum, the residue is dissolved in 200 ml of water and set at pH 7 by adding IR-120® cation exchanger (H+ form). Exchanger is filtered out and evaporated to the dry state in a vacuum. The residue is complexed without being further characterized.

Thin-layer system: n-butanol/aqueous ammonia/ethanol/water 12/6/3/3

Yield: 16 g c) Gd Complex of 10-(p-carboxybenzyl)-1,4,7-α,α',α"-trimethyl-1,4,7-tris(carboxy-methyl)-1,4,7,10-tetraazacyclododecane 11 g (20 mmol) of the ligand that is described in Example 8b is dissolved in 200 ml of water and 80 ml of isopropanol and acidified by adding 5 ml of acetic acid. 3.6 g (10 mmol) of gadolinium oxide is added and refluxed for 3 hours. After complexing is completed, it is set at pH 7.4 again with ammonia and chromatographed on silica gel (mobile solvent: dichloromethane/methanol/ammonia: 20/20/1). The fractions that contain the product are combined and added via an IR-120® cation exchange column (H+ form). The acidic eluate is freeze-dried.

Yield: 8.9 g (61% of theory) of a colorless powder. Water content (Karl-Fischer): 7.2% Elementary analysis (relative to anhydrous substance): Cld.: C, 44.37; H, 5.21; Gd, 23.23; N, 8.28. Fnd.: C, 44.12; H, 5.46; Gd, 22.93; N, 8.51.

Example 9 a) 10-(p-Methoxycarbonylbenzyl)-1,4,7-α,α',α"-tris(isopropyl)-1,4,7-tris(benzyloxycarbonyl-methyl)-1,4,7,10-tetraazacyclododecane 21.6 g (67.3 mmol) of the 1-(p-methoxycarbonylbenzyl)-1,4,7,10-tetraazacyclododecane that is described in Example 8a as an intermediate product and 60 ml (0.35 mol) of N-ethyldiisopropylamine in 200 ml of dichloromethane are added to 85.1 g (0.25 mol) of 2-(trifluoromethanesulfonyloxy)-isovaleric acid benzyl ester (Walker et al., Tetrahedron (1997), 53(43), 14591) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 48.5 g (81% of theory) of a colorless, crystalline powder Elementary analysis Cld.: C, 71.43; H, 7.92; N, 6.29. Fnd.: C, 71.12; H, 7.79; N, 6.55.

b) 10-(p-Carboxybenzyl)-1,4,7-α,α',α"-tris(isopropyl)-1,4,7-tris(carboxymethyl)-1,4,7,10-tetraazacyclododecane 26.7 g (30 mmol) of the title compound of Example 9a is dissolved in 400 ml of methanol, mixed with 100 ml of 15N sodium hydroxide solution, refluxed for 6 hours and stirred overnight at room temperature. After concentration by evaporation in a vacuum, the residue is dissolved in 200 ml of water and set at pH 7 by adding IR-120® cation exchanger (H$^+$ form). Exchanger is filtered out, and it is evaporated to the dry state in a vacuum. The residue is complexed without being further characterized.

Thin-layer system: n-butanol/aqueous ammonia/ethanol/water 12/6/3/3

Yield: 19 g c) Gd Complex of 10-p-carboxybenzyl)-1,4,7-α,α',α"-tris(isopropyl)-1,4,7-tris(carboxymethyl)-1,4,7,10-tetraazacyclododecane 12.6 g (20 mmol) of the ligand that is described in Example 9b is dissolved in 200 ml of water and 80 ml of isopropanol and acidified by adding 5 ml of acetic acid. 3.6 g (10 mmol) of gadolinium oxide is added, and it is refluxed for 3 hours. After complexing is completed, it is set at pH 7.4 again with ammonia, and it is chromatographed on silica gel (mobile solvent: dichloromethane/methanol/ammonia: 20/20/1). The fractions that contain the product are combined and added via an IR-120® cation exchange column (H$^+$ form). The acidic eluate is freeze-dried.

Yield: 10.9 g (65% of theory) of a colorless powder. Water content (Karl-Fischer): 9.0% Elementary analysis (relative to anhydrous substance): Cld.: C, 48.93; H, 6.23; Gd, 20.66; N, 7.36. Fnd.: C, 48.87; H, 6.01; Gd, 20.22; N, 7.59.

Example 10 a) 10-(p-Methoxycarbonylbenzyl)-1,4,7-α,α',α"-tris(cyclohexyl)-1,4,7-tris(benzyloxycarbonyl-methyl)-1,4,7,10-tetraazacyclododecane 21.6 g (67.3 mmol) of the 1-(p-methoxycarbonylbenzyl)-1,4,7,10-tetraazacyclododecane that is described in Example 8a as an intermediate product and 60 ml (0.35 mol) of N-ethyldiisopropylamine in 200 ml of dichloromethane are added to 95.1 g (0.25 mol) of 2-(trifluoromethanesulfonyloxy)-2-cyclohexylacetic acid benzyl ester (Qabar et al., Tetrahedron Letters (1998), 39(33), 5895) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 48.3 g (71% of theory) of a colorless, crystalline powder Elementary analysis: Cld.: C, 73.63; H, 8.17; N, 5.54. Fnd.: C, 73.42; H, 8.39; N, 5.75.

b) 10-(p-Carboxybenzyl)-1,4,7-α,α',α"-tris(cyclohexyl)-1,4,7-tris(carboxymethyl)-1,4,7,10-tetraazacyclododecane 30.3 g (30 mmol) of the title compound of Example 10a is dissolved in 400 ml of methanol, mixed with 100 ml of 15N sodium hydroxide solution, refluxed for 6 hours and stirred overnight at room temperature. After concentration by evaporation in a vacuum, the residue is dissolved in 200 ml of water and set at pH 7 by adding IR-120® cation exchanger (H$^+$ form). Exchanger is filtered out, and it is evaporated to the dry state in a vacuum. The residue is complexed without being further characterized.

Thin-layer system: n-butanol/aqueous ammonia/ethanol/water 12/6/3/3

Yield: 22.5 g c) Gd Complex of 10-(p-carboxybenzyl)-1,4,7-α,α',α"-tris(cyclohexyl)-1,4,7-tris(carboxymethyl)-1,4,7,10-tetraazacyclododecane 15.0 g (20 mmol) of the ligand that is described in Example 10b is dissolved in 200 ml of water and 80 ml of isopropanol and acidified by adding 5 ml of acetic acid. 3.6 g (10 mmol) of gadolinium oxide is added, and it is refluxed for 3 hours. After complexing is completed, it is set at pH 7.4 again with ammonia and chromatographed on silica gel (mobile solvent: dichloromethane/methanol/ammonia: 20/20/1). The fractions that contain the product are combined and evaporated to the dry state. The residue is taken up with formic acid and evaporated to the dry state several times with the addition of dichloromethane and then dried in a vacuum until a constant weight is reached.

Yield: 11.9 g (63% of theory) of a colorless powder. Water content (Karl-Fischer): 7.0% Elementary analysis (relative to anhydrous substance): Cld.: C, 54.52; H, 6.75; Gd, 17.85; N, 6.36. Fnd.: C, 54.19; H, 6.83; Gd, 17.61; N, 6.69.

Example 11 a) 10-(p-Methoxycarbonylbenzyl)-1,4,7-α,α',α"-triphenyl-1,4,7-tris(benzyloxycarbonyl-methyl)-1,4,7,10-tetraazacyclododecane 21.6 g (67.3 mmol) of 1-(p-methoxycarbonylbenzyl)-1,4,7,10-tetraazacyclododecane that is described in Example 8a as an intermediate product and 60 ml (0.35 mol) of N-ethyldiisopropylamine in 200 ml of dichloromethane are added to 93.6 g (0.25 mol) of 2-(trifluoromethanesulfonyloxy)-2-phenylacetic acid benzyl ester (Qabar et al., Tetrahedron Letters (1998), 39(33), 5895) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 50.8 g (76% of theory) of a colorless, crystalline powder Elementary analysis: Cld.: C, 74.98; H, 6.49; N, 5.64. Fnd.: C, 75.22; H, 6.61; N, 5.47.

b) 10-(p-Carboxybenzyl)-1,4,7-α,α',α"-triphenyl-1,4,7-tris(carboxymethyl)-1,4,7,10-tetraazacyclododecane 29.8 g (30 mmol) of the title compound of Example 11a is dissolved in 400 ml of methanol, mixed with 100 ml of 15N sodium hydroxide solution, refluxed for 6 hours and stirred overnight at room temperature. After concentration by evaporation in a vacuum, the residue is dissolved in 200 ml of water and set at pH 7 by adding IR-120® cation exchanger (H$^+$ form). Exchanger is filtered out, and it is evaporated to the dry state in a vacuum. The residue is complexed without being farther characterized.

Thin-layer system: n-butanol/aqueous ammonia/ethanol/water 12/6/3/3

Yield: 22.0 g c) Gd Complex of 10-(p-carboxybenzyl)-1,4,7-α,α',α"-triphenyl-1,4,7-tris(carboxymethyl)-1,4,7,10-tetraazacyclododecane 14.6 g (20 mmol) of the ligand that is described in Example 11b is dissolved in 200 ml of water and 80 ml of isopropanol, and it is acidified by adding 5 ml of acetic acid. 3.6 g (10 mmol) of gadolinium oxide is added, and it is refluxed for 3 hours. After complexing is completed, it is set at pH 7.4 again with ammonia and chromatographed on silica gel (mobile solvent: dichloromethane/methanol/ammonia: 20/20/1). The fractions that contain the product are combined and evaporated to the dry state. The residue is taken up with formic acid and evaporated to the dry state several times with the addition of dichloromethane and then dried in a vacuum until a constant weight is reached.

Yield: 13.1 g (70% of theory) of a colorless powder. Water content (Karl-Fischer): 8.1% Elementary analysis (relative to anhydrous substance): Cld.: C, 55.67; H, 4.79; Gd, 18.22; N, 6.49. Fnd.: C, 55.33; H, 4.97; Gd, 17.92; N, 6.54.

Example 12 a) 10-[4-(t-Butoxycarbonyl)-1-phenyl-2-oxo-3-azabutyl]-1,4,7-α,α',α"-triphenyl-1,4,7-tris-(benzyloxycarbonylmethyl)-1,4,7,10-tetraazacyclododecane 26.6 g (81.1 mmol) of N-[2-bromo-2-phenylacetyl]-glycine-t-butylester (Example 6a of WO 98/24775) is added to 27.9 g (162.2 mmol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: chloroform/methanol/aqueous 25% ammonia=10/5/1). The thus obtained 1-[4-(t-butoxycarbonyl)-1-phenyl-2-oxo-3-azabutyl]-1,4,7,10-tetraazacyclododecane (21.0 g; 50 mmol; 62% of theory) and 60 ml (0.35 mol) of N-ethyldiisopropylamine in 200 ml of dichloromethane are added to 74.9 g (0.2 mol) of 2-(trifluoromethanesulfonyloxy)-2-phenylacetic acid benzyl ester (Qabar et al., Tetrahedron Letters (1998), 39(33), 5895) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 30/1). The fractions that contain the product are combined and concentrated by evaporation.

Yield: 37.7 g (69% of theory) of a colorless, crystalline powder Elementary analysis: Cld.: C, 73.67; H, 6.74; N, 6.41. Fnd.: C, 73.44; H, 6.43; N, 6.79.

b) 10-(4-(t-Butoxycarbonyl-1-phenyl-2-oxo-3-azabutyl)-1,4,7-α,α',α"-triphenyl-1,4,7-tris(carboxymethyl)-1,4,7,10-tetraazacyclododecane 32.8 g (30 mmol) of the title compound of Example 12a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 24.8 g (quantitative) of a colorless powder Elementary analysis: Cld.: C, 67.22; H, 6.74; N, 8.52. Fnd.: C, 67.00; H, 6.85; N, 8.23.

c) Gd Complex of 10-(4-carboxy-1-phenyl-2-oxo-3-azabutyl)-1,4,7-α,α',α"-triphenyl-1,4,7-tris(carboxymethyl)-1,4,7,10-tetraazacyclododecane 16.4 g (20 mmol) of the t-butylester that is described in Example 12b is dissolved in very little trifluoroacetic acid, and it is stirred for 15 minutes at room temperature. After 250 ml of diethyl ether is added, it is stirred for 2 more hours, the precipitate is suctioned off, and it is dried in a vacuum. The thus obtained free ligand is dissolved in 200 ml of water and 80 ml of isopropanol, set at pH 7 with dilute ammonia and acidified by adding 5 ml of acetic acid. 3.6 g (10 mmol) of gadolinium oxide is added, and it is refluxed for 3 hours. After complexing is completed, it is set at pH 7.4 again with ammonia and chromatographed on silica gel (mobile solvent: dichloromethane/methanol/ammonia: 25/15/1). The fractions that contain the product are combined and added via an IR-120® cation exchange column (H$^+$ form). The acidic eluate is freeze-dried.

Yield: 11.7 g (59% of theory) of a colorless powder. Water content (Karl-Fischer): 7.5% Elementary analysis (relative to anhydrous substance): Cld.: C, 54.83; H, 4.82; Gd, 17.09; N, 7.61. Fnd.: C, 54.91; H, 4.67; Gd, 16.62; N, 7.33.

Example 13 a) 10-[4-(Benzyloxycarbonyl)-2-oxo-3-azabutyl]-1,4,7-α,α',α"-tris(isopropyl)-1,4,7-tris(benzyloxycarbonylmethyl)-1,4,7,10-tetraazacyclododecane 23.2 g (81.1 mmol) of 2-bromoacetylglycine-benzyl ester (Teger-Nilsson et al., WO 93/11152, page 38) is added to 34.4 g (0.2 mol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: chloroform/methanol/aqueous 25% ammonia=10/5/1). The thus obtained 1-[4-(benzyloxycarbonyl)-2-oxo-3-azabutyl]-1,4,7,10-tetraazacyclododecane (19.6 g; 50 mmol; 62% of theory) and 60 ml (0.35 mol) of N-ethyldiisopropylamine in 200 ml of dichloromethane are added to 68.1 g (0.2 mol) of 2-(trifluoromethanesulfonyloxy)-isovaleric acid benzyl ester (Walker et al., Tetrahedron (1997), 53/43), 14591) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 37.0 g (78% of theory) of a colorless, crystalline powder Elementary analysis: Cld.: C, 69.67; H, 7.76; N, 7.39. Fnd.: C, 69.51; H, 7.88; N, 7.39.

b) 10-(4-Carboxy-2-oxo-3-azabutyl)-1,4,7-α,α',α"-tris(isopropyl)-1,4,7-tris(carboxymethyl)-1,4,7,10-tetraazacyclododecane 28.4 g (30 mmol) of the title compound of Example 13a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 17.7 g (quantitative) of a colorless powder Elementary analysis: Cld.: C, 55.18; H, 8.40; N, 11.92. Fnd.: C, 54.97; H, 8.70; N, 11.88.

c) Gd Complex of 10-(4-carboxy-2-oxo-3-azabutyl)-1,4,7-α,α',α"-tris(isopropyl)-1,4,7-tris(carboxymethyl)-1,4,7,10-tetraazacyclododecane 11.8 g (20 mmol) of the ligand that is described in Example 13b is dissolved in 200 ml of water and 80 ml of isopropanol and acidified by adding 5 ml of acetic acid. 3.6 g (10 mmol) of gadolinium oxide is added, and it is refluxed for 3 hours. After complexing is completed, it is set at pH 7.4 with ammonia and chromatographed on silica gel (mobile solvent: dichloromethane/methanol/ammonia: 20/20/1). The fractions that contain the product are combined and added via an IR-120® cation exchange column (H+ form). The acidic eluate is freeze-dried.

Yield: 12.1 g (75% of theory) of a colorless powder. Water content (Karl-Fischer): 8.0% Elementary analysis (relative to anhydrous substance): Cld.: C, 43.71; H, 6.25; Gd, 21.19; N, 9.44. Fnd.: C, 43.90; H, 6.40; Gd, 20.80; N, 9.33.

Example 14 a) 10-[4-(Benzyloxycarbonyl)-2-oxo-3-azabutyl]-1,4,7-α,α',α"-tris(cyclohexyl)-1,4,7-tris-(benzyloxycarbonylmethyl)-1,4,7,10-tetraazacyclododecane 18.9 g (50 mmol) of 1-[4-(benzyloxycarbonyl)-2-oxo-3-azabutyl]-1,4,7,10-tetraazacyclododecane that is described in Example 13a as an intermediate product and 60 ml (0.35 mol) of N-ethyldiisopropylamine in 200 ml of dichloromethane are added to 76.1 g (0.2 mol) of 2-(trifluoromethanesulfonyloxy)-2-cyclohexylacetic acid benzyl ester (Qabar et al., Tetrahedron Letters (1998), 39(33), 5895) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 38.5 g (72% of theory) of a colorless, crystalline powder Elementary analysis: Cld.: C, 71.95; H, 8.02; N, 6.56. Fnd.: C, 71.90; H, 8.21; N, 6.73.

b) 10-(4-Carboxy-2-oxo-3-azabutyl)-1,4,7-α,α',α"-tris(cyclohexyl)-1,4,7-tris(carboxymethyl)-1,4,7,10-tetraazacyclododecane 32.1 g (30 mmol) of the title compound of Example 14a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 21.2 g (quantitative) of a colorless powder Elementary analysis: Cld.: C, 61.08; H, 8.69; N, 9.89. Fnd.: C, 61.27; H, 8.55; N, 9.41.

c) Gd Complex of 10-(4-carboxy-2-oxo-3-azabutyl)-1,4,7-α,α',α"-tris(cyclohexyl)-1,4,7-tris(carboxymethyl)-1,4,7,10-tetraazacyclododecane 14.2 g (20 mmol) of the ligand that is described in Example 14b is dissolved in 150 ml of water and 150 ml of isopropanol, and it is acidified by adding 5 ml of acetic acid. 3.6 g (10 mmol) of gadolinium oxide is added, and it is refluxed for 8 hours. After complexing is completed, it is set at pH 7.4 again with ammonia and chromatographed on silica gel (mobile solvent: dichloromethane/methanol/ammonia: 20/20/1). The fractions that contain the product are combined and evaporated to the dry state. The residue is taken up with formic acid and evaporated to the dry state several times with the addition of dichloromethane and then dried in a vacuum until a constant weight is reached.

Yield: 13.5 g (71% of theory) of a colorless powder. Water content (Karl-Fischer): 9.0% Elementary analysis (relative to anhydrous substance): Cld.: C, 50.15; H, 6.78; Gd, 18.24; N, 8.12. Fnd.: C, 49.92; H, 6.51; Gd, 18.01; N, 8.31.

Example 15 a) 10-[4-(Benzyloxycarbonyl)-1-methyl-2-oxo-3-azabutyl]-2,5,8,11-tetramethyl-1,4,7,10-tetraazacyclododecane-1,4,7-triacetic acid-tri-t-butylester, sodium bromide complex 0.50 g (1.67 mmol) of 2-bromo-propionylglycine-benzyl ester (Example 1e of WO 98/24774) is added to 1.14 g (5 mmol) of 2,5,8,11-tetramethyl-1,4,7,10-tetraazacyclododecane (Petrov et al., DE 19608307; Ranganathan et al., WO 95/31444), dissolved in 10 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: chloroform/methanol/aqueous 25% ammonia=10/5/1). 822 mg (4.2 mmol) of bromoacetic acid-tert-butyl ester is added to the thus obtained 1-[4-(benzyloxycarbonyl)-1-methyl-2-oxo-3-azabutyl]-2,5,8,11-tetramethyl-1,4,7,10-tetraazacyclododecane (0.70 g; 1.27 mmol; 76% of theory) and 541 mg (5.1 mmol) of sodium carbonate in 5 ml of acetonitrile, and it is stirred for 12 hours at 60° C. It is cooled to 0° C., and salts are filtered out. The filtrate is evaporated to the dry state, and the residue is chromatographed on silica gel (mobile solvent: methylene chloride/methanol=20:1).

Yield: 964 mg (85% of theory) of a colorless solid Elementary analysis: Cld.: C, 56.49; H, 8.01; N, 7.84; Na, 2.57; Br, 8.95. Fnd.: C, 56.37; H, 7.88; N, 7.61; Na, 2.33; Br, 8.59.

b) 10-(4-Carboxy-1-methyl-2-oxo-3-azabutyl)-2,5,8,
11-tetramethyl-1,4,7,10-tetraazacyclododecane-1,4,
7-triacetic acid-tri-tert-butyl ester (sodium bromide
complex)

893 mg (1.0 mmol) of the title compound of Example 15a is dissolved in 10 ml of isopropanol, and a spatula tip full of palladium catalyst (10% Pd/C) is added. It is hydrogenated overnight at room temperature. Catalyst is filtered out, and the filtrate is evaporated to the dry state. The residue is recrystallized from dioxane.

Yield: 562 mg (70% of theory) of a crystalline solid
Elementary analysis: Cld.: C, 52.36; H, 8.16; N, 8.72; Na, 2.86; Br, 9.95. Fnd.: C, 52.51; H, 8.30; N, 8.93; Na, 2.71; Br, 9.44.

c) Gadolinium complex of 10-(4-carboxy-1-methyl-
2-oxo-3-azabutyl)-2,5,8,11-tetramethyl-1,4,7,10-
tetraazacyclododecane-1,4,7-triacetic acid 803 mg (1.0 mmol) of the title compound of Example 15b is dissolved in 5 ml of trifluoroacetic acid and stirred for 3 hours at room temperature. It is evaporated to the dry state, the residue is taken up in 300 ml of water, and the solution is added to a column, filled with Reillex® 425 PVP. It is eluted with water. The product-containing fractions are combined and evaporated to the dry state (446 mg; 0.84 mmol) and again dissolved in 4 ml of water. 152 mg (0.42 mmol) of gadolinium oxide is added, and it is heated for 3 hours to 90° C. It is evaporated to the dry state (vacuum), and the residue is crystallized from 90% aqueous ethanol. The crystals are suctioned off, washed once with ethanol, then with acetone and finally with dimethyl ether and dried in a vacuum furnace at 130° C. (24 hours).

Yield: 469 mg (65% of theory) of a colorless, crystalline powder Water content: 5% Elementary analysis (relative to anhydrous substance): Cld.: C, 40.28; H, 5.58; N, 10.21; Gd, 22.93. Fnd.: C, 40.06; H, 5.75; N, 10.43; Gd, 22.40.

Example 16

Gd Complex of 10-[8-(N-maleimido)-1-methyl-2,5-
dioxo-3,6-diazaoctyl]-1,4,7-α,α',α"-tris-(isopropyl)-
1,4,7-tris(carboxymethyl)-1,4,7,10-tetraazacy-
clododecane 2.27 g (3 mmol) of the Gd complex acid that is described in Example 2 is dissolved in 15 ml of DMF, mixed with 380 mg (3.3 mmol) of N-hydroxysuccinimide and 681 mg (3.3 mmol) of dicyclohexylcarbodiimide while being cooled with ice and preactivated for 1 hour in ice. Then, a mixture that consists of 839 mg (3.3 mmol) of N-(2-aminoethyl) maleimide trifluoroacetate salt (Arano et al., J. Med. Chem., 1996, 39, 3458) and 0.7 ml (4 mmol) of N,N-diisopropyl-ethyl-amine in 10 ml of DMF is added and stirred overnight at room temperature. The reaction mixture is cooled again in an ice bath, filtered, and the filtrate is evaporated to the dry state in a vacuum. The residue is chromatographed on silica gel (mobile solvent: dichloromethane/methanol: 1/1).

Yield: 997 mg (35% of theory) Water content (Karl-Fischer): 7.5% Elementary analysis (relative to anhydrous substance): Cld.: C, 46.51; H, 6.20; Gd, 17.91; N, 11.17. Fnd.: C, 46.28; H, 6.44; Gd, 17.31; N, 11.26.

Example 17

Gd Complex of 10-[8-(N-maleimido)-1-methyl-2,5-
dioxo-3,6-diazaoctyl]-1,4,7-α,α',α"-tris-(cyclo-
hexyl)-1,4,7-tris(carboxymethyl)-1,4,7,10-tetraaza-
cyclododecane 2.63 g (3 mmol) of the Gd complex acid that is described in Example 3 is dissolved in 15 ml of DMF, mixed with 380 mg (3.3 mmol) of N-hydroxysuccinimide and 681 mg (3.3 mmol) of dicyclohexylcarbodiimide while being cooled with ice, and preactivated for 1 hour in ice. Then, a mixture that consists of 839 mg (3.3 mmol) of N-(2-aminoethyl) maleimide trifluoroacetate salt (Arano et al., J. Med. Chem., 1996, 39, 3458) and 0.7 ml (4 mmol) of N,N-diisopropyl-ethylamine in 10 ml of DMF is added and stirred overnight at room temperature. The reaction mixture is cooled again in an ice bath, filtered, and the filtrate is evaporated to the dry state in a vacuum. The residue is chromatographed on silica gel (mobile solvent: dichloromethane/methanol: 1/1).

Yield: 1.24 g (39% of theory) Water content (Karl-Fischer): 6.0% Elementary analysis (relative to anhydrous substance): Cld.: C, 51.74; H, 6.66; Gd, 15.75; N, 9.82. Fnd.: C, 51.77; H, 6.41; Gd, 15.25; N, 10.02.

Example 18 a) (3-Bromo-2-oxo-pyrrolidin-1-yl)acetic acid
benzyl ester 67.7 g (0.2 mol) of glycinebenzyl ester tosylate and 61.2 ml (0.44 mol) of triethylamine are dissolved in 200 ml of methylene chloride and added in drops at 0° C. to a solution of 52.9 g (0.2 mol) of 2,4-dibromobutyric acid chloride (Gramain et al. Synth. Commun. (1997), (27), 1827) in 200 ml of methylene chloride within 45 minutes, and it is stirred for 18 hours at room temperature. The reaction mixture is now added in drops at 0° C. to a solution of 400 ml of aqueous 32% sodium hydroxide and 2 g of tetrabutylam-monium hydrogen carbonate (about 15 minutes), and it is stirred for 30 minutes. Then, the phases are separated, and the aqueous phase is extracted three times with 200 ml each of dichloromethane. The organic phases are dried on sodium sulfate, the solution is evaporated to the dry state and chromatographed on silica gel (methylene chloride). The fractions that contain the product are combined and concentrated by evaporation.

Yield: 29.3 g (47% of theory) Elementary analysis: Cld.: C, 50.02; H, 4.52; N, 4.49. Fnd.: C, 50.34; H, 4.44; N, 4.41.

b) 10-[1-(Benzyloxycarbonylmethyl)-2-oxo-pyrroli-
din-3-yl]-1,4,7-α,α',α"-trimethyl-1,4,7-tris-(benzy-
loxycarbonylmethyl)-1,4,7,10-tetraazacyclodode-
cane 20.7 g (66.3 mmol) of (3-bromo-2-oxo-pyrrolidin-1-yl) acetic acid benzyl ester is added to 28.7 g (165.8 mmol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: chloroform/methanol/aqueous 25% ammonia=10/5/1). The thus obtained 1-[1-(benzyloxy-carbonylmethyl)-2-oxo-pyrrolidin-3-yl]-1,4,7,10-tetraaza-cyclododecane (20.9 g; 51.8 mmol; 78% of theory) and 60 ml (0.35 mol) of N-ethyldiisopropylamine in 200 ml of dichloromethane are added to 62.45 g (0.2 mol) of 2-(trifluoromethanesulfonyloxy)propanoic acid benzyl ester (Kitazaki et al., Chem. Pharm. Bull. (1999), 47(3), 360) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 32.7 g (71% of theory) of a colorless, crystalline powder Elementary analysis: Clod.: C, 68.82; H, 7.13; N, 7.87. Find.: C, 68.54; H, 7.28; N, 8.01.

c) 10-[1-(Carboxymethyl)-2-oxo-pyrrolidin-3-yl]-1, 4,7-α,α',α"-trimethyl-1,4,7-tris(carboxymethyl)-1,4, 7,10-tetraazacyclododecane 26.7 g (30 mmol) of the title compound of Example 18b is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 15.8 g (quantitative) of a colorless powder Elementary analysis: Cld.: C, 52.16; H, 7.42; N, 13.22. Fnd.: C, 52.32; H, 7.35; N, 13.11.

d) Gd Complex of 10-[1-(carboxymethyl)-2-oxo-pyrrolidin-3-yl]-1,4,7-α,α',α"-trimethyl-1,4,7-tris(carboxymethyl)-1,4,7,10-tetraazacyclododecane 10.6 g (20 mmol) of the ligand that is described in Example 18c is dissolved in 200 ml of water and 80 ml of isopropanol and acidified by adding 5 ml of acetic acid. 3.6 g (10 mmol) of gadolinium oxide is added, and it is refluxed for 3 hours. After complexing is completed, it is set at pH 7.4 again with ammonia and chromatographed on silica gel (mobile solvent: dichloromethane/methanol/ammonia: 20/20/1). The fractions that contain the product are combined and added via an IR-120® cation exchange column (H⁺ form). The acidic elate is freeze-dried.

Yield: 9.7 g (67% of theory) of a colorless powder. Water content (Karl-Fischer): 8.3% Elementary analysis (relative to anhydrous substance): Cld.: C, 40.40; H, 5.31; Gd, 23.00; N, 10.24. Fnd.: C, 39.99; H, 5.55; Gd, 22.93; N, 10.45.

Example 19 a) 10-[1-(Benzyloxycarbonylmethyl)-2-oxo-pyrrolidin-3-yl]-1,4,7-α,α',α"-tris(isopropyl)-1,4,7-tris(benzyloxycarbonylmethyl)-1,4,7,10-tetraazacyclododecane 20.2 g (50 mmol) of 1-[1-(benzyloxycarbonylmethyl)-2-oxo-pyrolidin-3-yl]-1,4,7,10-tetraazacyclododecane that is described in Example 18b as an intermediate product and 60 ml (0.35 mol) of N-ethyldiisopropylamine in 200 ml of dichloromethane are added to 68.1 g (0.2 mol) of 2-(trifluoromethanesulfonyloxy)-isovaleric acid benzyl ester (Walker et al., Tetrahedron (1997), 53(43), 14591) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 34.1 g (70% of theory) of a colorless, crystalline powder Elementary analysis: Cld.: C, 70.27; H, 7.76; N, 7.19. Fnd.: C, 70.45; H, 7.61; N, 7.11.

b) 10-[1-(Carboxymethyl)-2-oxo-pyrrolidin-3-yl]-1, 4,7-α,α',α"-tris(isopropyl)-1,4,7-tris(carboxymethyl)-1,4,7,10-tetraazacyclododecane 29.2 g (30 mmol) of the title compound of Example 19a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 18.4 g (quantitative) of a colorless powder Elementary analysis: Cld.: C, 56.75; H, 8.38; N, 11.41. Fnd.: C, 56.89; H, 8.31; N, 11.37.

c) Gd Complex of 10-[1-(carboxymethyl)-2-oxo-pyrrolidin-3-yl]-1,4,7-α,α',α"-tris(isopropyl)-1,4,7-tris(carboxymethyl)-1,4,7,10-tetraazacyclododecane 12.3 g (20 mmol) of the ligand that is described in Example 19b is dissolved in 200 ml of water and 80 ml of isopropanol and acidified by adding 5 ml of acetic acid. 3.6 g (10 mmol) of gadolinium oxide is added, and it is refluxed for 3 hours. After complexing is completed, it is set at pH 7.4 with ammonia and chromatographed on silica gel (mobile solvent: dichloromethane/methanol/ammonia: 20/20/1). The fractions that contain the product are combined and added via an IR-120® cation exchange column (H⁺ form). The acidic eluate is freeze-dried.

Yield: 11.9 g (75% of theory) of a colorless powder. Water content (Karl-Fischer): 8.2% Elementary analysis (relative to anhydrous substance): Cld.: C, 45.36; H, 6.30; Gd, 20.48; N, 9.12. Fnd.: C, 45.89; H, 6.22; Gd, 20.23; N, 9.01.

The Dy complex of 10-[1-(carboxymethyl)-2-oxo-pyrrolidin-3-yl]-1,4,7-α,α',α"-tris(isopropyl)-1,4,7-tris(carboxymethyl)-1,4,7,10-tetraazacyclododecane is obtained analogously with use of 12.3 g (20 mmol) of the ligand that is described in Example 19b and 3.73 g (10 mmol) of dysprosium oxide instead of gadolinium oxide.

Yield: 11.4 g (71% of theory) of a colorless powder. Water content (Karl-Fischer): 8.0% Elementary analysis (relative to anhydrous substance): Cld.: C, 45.05; H, 6.26; Dy, 21.02; N, 9.06. Fnd.: C, 45.35; H, 6.22; Dy, 20.88; N, 9.04.

Example 20 a) 10-[1-(Benzyloxycarbonylmethyl)-2-oxo-pyrrolidin-3-yl]-1,4,7-α,α',α"-tris(cyclohexyl)-1,4,7-tris (benzyloxycarbonylmethyl)-1,4,7,10-tetraazacyclododecane 20.2 g (50 mmol) of 1-[1-(benzyloxycarbonylmethyl)-2-oxo-pyrolidin-3-yl]-1,4,7,10-tetraazacyclododecane that is described in Example 18b as an intermediate product and 60 ml (0.35 mol) of N-ethyldiisopropylamine in 200 ml of dichloromethane are added to 76.1 g (0.2 mol) of 2-(trifluoromethanesulfonyloxy)-2-cyclohexylacetic acid benzyl ester (Qabar et al., Tetrahedron Letters (1998), 39(33), 5895) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 37.2 g (68% of theory) of a colorless, crystalline powder Elementary analysis: Cld.: C, 72.43; H, 8.01; N, 6.40. Fnd.: C, 72.55; H, 7.98; N, 6.35.

b) 10-[1-(Carboxymethyl)-2-oxo-pyrrolidin-3-yl]-1,4,7-α,α',α''-tris(cyclohexyl)-1,4,7-tris(carboxymethyl)-1,4,7,10-tetraazacyclododecane 32.8 g (30 mmol) of the title compound of Example 20a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 22.0 g (quantitative) of a colorless powder Elementary analysis: Cld.: C, 62.19; H, 8.65; N, 9.54. Fnd.: C, 62.44; H, 8.56; N, 9.46.

c) Gd Complex of 10-[1-(carboxymethyl)-2-oxo-pyrrolidin-3-yl]-1,4,7-α,α',α''-tris(cyclohexyl)-1,4,7-tris(carboxymethyl)-1,4,7,10-tetraazacyclododecane 14.6 g (20 mmol) of the ligand that is described in Example 20b is dissolved in 150 ml of water and 150 ml of isopropanol and acidified by adding 5 ml of acetic acid. 3.6 g (10 mmol) of gadolinium oxide is added, and it is refluxed for 8 hours. After complexing is completed, it is set at pH 7.4 again with ammonia and chromatographed on silica gel (mobile solvent: dichloromethane/methanol/ammonia: 20/20/1). The fractions that contain the product are combined and evaporated to the dry state. The residue is taken up with formic acid and evaporated to the dry state several times with the addition of dichloromethane, and then it is dried in a vacuum until a constant weight is reached.

Yield: 12.1 g (65% of theory) of a colorless powder. Water content (Karl-Fischer): 7.0% Elementary analysis (relative to anhydrous substance): Cld.: C, 51.39; H, 6.81; Gd, 17.70; N, 7.89. Fnd.: C, 51.64; H, 6.77; Gd, 17.44; N, 7.77.

Example 21 a) (3-Bromo-2-oxo-pyrrolidin-1-yl)benzoic acid benzyl ester 45.5 g (0.2 mol) of 4-aminobenzoic acid benzyl ester and 30.6 ml (0.22 mol) of triethylamine are dissolved in 200 ml of methylene chloride and added in drops at 0° C. to a solution of 52.9 g (0.2 mol) of 2,4-dibromobutyric acid chloride (Gramin et al. Synth. Commun. (1997), (27), 1827) in 200 ml of methylene chloride within 45 minutes, and it is stirred for 18 hours at room temperature. The reaction mixture is now added in drops at 0° C. to a solution of 400 ml of aqueous 32% sodium hydroxide and 2 g of tetrabutylammonium hydrogen carbonate (about 15 minutes), and it is stirred for 30 minutes. Then, the phases are separated, and the aqueous phase is extracted three times with 200 ml of dichloromethane each. The organic phases are dried on sodium sulfate, the solution is evaporated to the dry state and chromatographed on silica gel (methylene chloride). The fractions that contain the product are combined and concentrated by evaporation.

Yield: 38.2 g (51% of theory) Elementary analysis: Cld.: C, 57.77; H, 4.31; N, 3.74. Fnd.: C, 57.99; H, 4.27; N, 3.66.

b) 10-[1-(4-Benzyloxycarbonylphenyl)-2-oxo-pyrrolidin-3-yl]-1,4,7-α,α',α''-trimethyl-1,4,7-tris-(benzyloxycarbonylmethyl)-1,4,7,10-tetraazacyclododecane 26.9 g (71.9 mmol) of (3-bromo-2-oxo-pyrrolidin-1-yl) benzoic acid benzyl ester is added to 31.2 g (180 mmol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: chloroform/methanol/aqueous 25% ammonia=10/5/1). The thus obtained 1-[1-(4-benzyloxycarbonylphenyl)-2-oxo-pyrrolidin-3-yl]-1,4,7,10-tetraazacyclododecane (26.1 g; 56.1 mmol; 78% of theory) and 60 ml (0.35 mol) of N-ethyldiisopropylamine in 200 ml of dichloromethane are added to 62.45 g (0.2 mol) of 2-(trifluoromethanesulfonyloxy)propanoic acid benzyl ester (Kitazaki et al., Chem. Pharm. Bull. (1999), 47(3), 360) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 36.3 g (68% of theory) of a colorless, crystalline powder Elementary analysis: Cld.: C, 70.64; H, 6.88; N, 7.36. Fnd.: C, 70.89; H, 6.81; N, 7.29.

c) 10-[1-(4-Carboxyphenyl)-2-oxo-pyrrolidin-3-yl]-1,4,7-α,α',α''-trimethyl-1,4,7-tris(carboxymethyl)-1,4,7,10-tetraazacyclododecane 28.6 g (30 mmol) of the title compound of Example 21b is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 17.7 g (quantitative) of a colorless powder Elementary analysis: Cld.: C, 56.84; H, 6.98; N, 11.84. Fnd.: C, 57.04; H, 6.91; N, 11.79.

d) Gd Complex of 10-[1-(4-carboxyphenyl)-2-oxo-pyrrolidin-3-yl]-1,4,7-α,α',α''-trimethyl-1,4,7-tris(carboxymethyl)-1,4,7,10-tetraazacyclododecane 11.8 g (20 mmol) of the ligand that is described in Example 21c is dissolved in 200 ml of water and 80 ml of isopropanol, and it is acidified by adding 5 ml of acetic acid. 3.6 g (10 mmol) of gadolinium oxide is added, and it is refluxed for 3 hours. After complexing is completed, it is set at pH 7.4 again with ammonia and chromatographed on silica gel (mobile solvent: dichloromethane/methanol/ammonia: 20/20/1). The fractions that contain the product are combined and added via an IR-120® cation exchange column (H+ form). The acidic eluate is freeze-dried.

Yield: 11.1 g (71% of theory) of a colorless powder. Water content (Karl-Fischer): 7.5% Elementary analysis (relative to anhydrous substance): Cld.: C, 45.09; H, 5.13; Gd, 21.08; N, 9.39. Fnd.: C, 45.45; H, 5.11; Gd, 20.78; N, 9.40.

Example 22 a) 10-[1-(4-Benzyloxycarbonylphenyl)-2-oxo-pyrrolidin-3-yl]-1,4,7-α,α',α''-tris(isopropyl)-1,4,7-tris(benzyloxycarbonylmethyl)-1,4,7,10-tetraazacyclododecane 23.3 g (50 mmol) of 1-[1-(4-benzyloxycarbonylphenyl)-2-oxo-pyrrolidin-3-yl]-1,4,7,10-tetraazacyclododecane that is described in Example 21b as an intermediate product and 60 ml (0.35 mol) of N-ethyldiisopropylamine in 200 ml of dichloromethane are added to 68.1 g (0.2 mol) of 2-(trifluoromethanesulfonyloxy)-isovaleric acid benzyl ester (Walker et al., Tetrahedron (1997), 53(43), 14591) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 35.3 g (68% of theory) of a colorless, crystalline powder Elementary analysis: Cld.: C, 71.86; H, 7.49; N, 6.76. Fnd.: C, 71.99; H, 7.46; N, 6.71.

b) 10-[1-(4-Carboxyphenyl)-2-oxo-pyrrolidin-3-yl]-1,4,7-α,α',α''-tris(isopropyl)-1,4,7-tris(carboxymethyl)-1,4,7,10-tetraazacyclododecane 31.1 g (30 mmol) of the title compound of Example 22a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 20.2 g (quantitative) of a colorless powder Elementary analysis: Cld.: C, 60.43; H, 7.90; N, 10.36. Fnd.: C, 60.59; H, 7.82; N, 10.31.

c) Gd Complex of 10-[1-(4-carboxyphenyl)-2-oxo-pyrrolidin-3-yl]-1,4,7-α,α',α''-tris(isopropyl)-1,4,7-tris(carboxymethyl)-1,4,7,10-tetraazacyclododecane 13.5 g (20 mmol) of the ligand that is described in Example 22b is dissolved in 200 ml of water and 80 ml of isopropanol, and it is acidified by adding 5 ml of acetic acid. 3.6 g (10 mmol) of gadolinium oxide is added, and it is refluxed for 3 hours. After complexing is completed, it is set at pH 7.4 with ammonia and chromatographed on silica gel (mobile solvent: dichloromethane/methanol/ammonia: 20/20/1). The fractions that contain the product are combined and added via an R-120® cation exchange column ($H^+$ form). The acidic eluate is freeze-dried.

Yield: 12.4 g (72% of theory) of a colorless powder. Water content (Karl-Fischer): 7.8% Elementary analysis (relative to anhydrous substance): Cld.: C, 49.20; H, 6.07; Gd, 18.94; N, 8.44. Fnd.: C, 49.51; H, 6.04; Gd, 18.71; N, 8.45.

The Dy complex of 10-[1-(4-carboxyphenyl)-2-oxo-pyrrolidin-3-yl]-1,4,7-α,α',α''-tris(isopropyl)-1,4,7-tris(carboxymethyl)-1,4,7,10-tetraazacyclododecane is analogously obtained with use of 13.5 g (20 mmol) of the ligand that is described in Example 22b and 3.73 g (10 mmol) of dysprosium oxide instead of gadolinium oxide.

Yield: 13.0 g (75% of theory) of a colorless powder. Water content (Karl-Fischer): 7.5% Elementary analysis (relative to anhydrous substance): Cld.: C, 48.89; H, 6.03; Dy, 19.45; N, 8.38. Fnd.: C, 49.11; H, 6.04; Dy, 19.22; N, 8.36.

Example 23 a) 10-[1-(4-Benzyloxycarbonylphenyl)-2-oxo-pyrrolidin-3-yl]-1,4,7-α,α',α''-tris(cyclohexyl)-1,4,7-tris(benzyloxycarbonylmethyl)-1,4,7,10-tetraazacyclododecane 23.3 g (50 mmol) of 1-[1-(4-benzyloxycarbonylphenyl)-2-oxo-pyrrolidin-3-yl]-1,4,7,10-tetraazacyclododecane that is described in Example 21b as an intermediate product and 60 ml (0.35 mol) of N-ethylodiisopropylamine in 200 ml of dichloromethane are added to 76.1 g (0.2 mol) of 2-(trifluoromethanesulfonyloxy)-2-cyclohexyalacetic acid benzyl ester (Qabar et al., Tetrahedron Letters (1998), 39(33), 5895) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 41.1 g (71% of theory) of a colorless, crystalline powder Elementary analysis: Cld.: C, 73.74; H, 7.76; N, 6.06. Fnd.: C, 73.91; H, 7.69; N, 6.01.

b) 10-[1-(4-Carboxyphenyl)-2-oxo-pyrrolidin-3-yl]-1,4,7-α,α',α''-tris(cyclohexyl)-1,4,7-tris-(carboxymethyl)-1,4,7,10-tetraazacyclododecane 34.7 g (30 mmol) of the title compound of Example 23a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 23.8 g (quantitative) of a colorless powder Elementary analysis: Cld.: C, 64.88; H, 8.23; N, 8.80. Fnd.: C, 65.04; H, 8.19; N, 8.70.

c) Gd Complex of 10-[1-(4-carboxyphenyl)-2-oxo-pyrrolidin-3-yl]-1,4,7-α,α',α''-tris(cyclohexyl)-1,4,7-tris(carboxymethyl)-1,4,7,10-tetraazacyclododecane 15.9 g (20 mmol) of the ligand that is described in Example 23b is dissolved in 150 ml of water and 150 ml of isopropanol and acidified by adding 5 ml of acetic acid. 3.6 g (10 mmol) of gadolinium oxide is added, and it is refluxed for 8 hours. After complexing is completed, it is set at pH 7.4 again with ammonia and chromatographed on silica gel (mobile solvent: dichloromethane/methanol/ammonia: 20/20/1). The fractions that contain the product are combined and evaporated to the dry state. The residue is taken up with formic acid and evaporated to the dry state several times with the addition of dichloromethane and then dried in a vacuum until a constant weight is reached.

Yield: 12.9 g (65% of theory) of a colorless powder. Water content (Karl-Fischer): 7.0% Elementary analysis (relative to anhydrous substance): Cld.: C, 54.35; H, 6.58; Gd, 16.55; N, 7.37. Fnd.: C, 54.66; H, 6.57; Gd, 16.32; N, 7.32.

Example 24 a) (3-Bromo-2-oxo-piperidin-1-yl)acetic acid benzyl ester 67.7 g (0.2 mol) of glycine benzyl ester tosylate and 61.2 ml (0.44 mol) of triethylamine are dissolved in 200 ml of methylene chloride and added in drops at 0° C. to a solution of 55.7 g (0.2 mol) of 2,5-dibromovaleric acid chloride (Okawara et al. Chem. Pharm. Bull. (1982), (30), 1225) in 200 ml of methylene chloride within 45 minutes, and it is stirred for 18 hours at room temperature. The reaction mixture is now added in drops at 0° C. to a solution of 400 ml of aqueous 32% sodium hydroxide and 2 g of tetrabutylammonium hydrogen carbonate (about 15 minutes), and it is stirred for 30 minutes. Then, the phases are separated, and the aqueous phase is extracted three times with 200 ml of dichloromethane each. The organic phases are dried on sodium sulfate, the solution is evaporated to the dry state and chromatographed on silica gel (methylene chloride). The fractions that contain the product are combined and concentrated by evaporation.

Yield: 33.2 g (51% of theory) Elementary analysis: Cld.: C, 51.55; H, 4.94; N, 4.29. Fnd.: C, 51.86; H, 4.91; N, 4.18.

b) 10-[1-(Benzyloxycarbonylmethyl)-2-oxo-piperidin-3-yl]-1,4,7-α,α',α"-trimethyl-1,4,7-tris-(benzyloxycarbonylmethyl)-1,4,7,10-tetraazacyclododecane 18.9 g (58 mmol) of (3-bromo-2-oxo-piperidin-1-yl)acetic acid benzyl ester is added to 30.3 g (175 mmol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: chloroform/methanol/aqueous 25% ammonia=10/5/1). The thus obtained 1-[1-(benzyloxycarbonylmethyl)-2-oxo-piperidin-3-yl]-1,4,7,10-tetraazacyclododecane (20.3 g; 48.6 mol; 84% of theory) and 60 ml (0.35 mol) of N-ethyldiisopropylamine in 200 ml of dichloromethane are added to 62.45 g (0.2 mol) of 2-(trifluoromethanesulfonyloxy)propanoic acid benzyl ester (Kitazaki et al., Chem. Pharm. Bull. (1999), 47(3), 360) in 400 ml of dichloromethane, and it is stirred for 6 hours under reflux and then overnight at room temperature. It is extracted three times with 500 ml of water each, and the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 32.5 g (74% of theory) of a colorless, crystalline powder Elementary analysis: Cld.: C, 69.08; H, 7.25; N, 7.75. Fnd.: C, 69.34; H, 7.19; N, 7.66.

c) 10-[1-(Carboxymethyl)-2-oxo-piperidin-3-yl]-1,4,7-α,α',α"-trimethyl-1,4,7-tris(carboxymethyl)-1,4,7,10-tetraazacyclododecane 27.1 g (30 mmol) of the title compound of Example 24b is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 16.3 g (quantitative) of a colorless powder Elementary analysis: Cld.: C, 53.03; H, 7.60; N, 12.88. Fnd.: C, 53.34; H, 7.54; N, 12.79.

d) Gd Complex of 10-[1-(Carboxymethyl)-2-oxo-piperidin-3-yl]-1,4,7-α,α',α"-trimethyl-1,4,7-tris(carboxymethyl)-1,4,7,10-tetraazacyclododecane 10.9 g (20 mmol) of the ligand that is described in Example 24c is dissolved in 200 ml of water and 80 ml of isopropanol, and it is acidified by adding 5 ml of acetic acid. 3.6 g (10 mmol) of gadolinium oxide is added and refluxed for 3 hours. After complexing is completed, it is set at pH 7.4 again with ammonia and chromatographed on silica gel (mobile solvent: dichloromethane/methanol/ammonia: 20/20/1). The fractions that contain the product are combined and added via an IR-120® cation exchange column (H+ form). The acidic eluate is freeze-dried.

Yield: 9.6 g (65% of theory) of a colorless powder. Water content (Karl-Fischer): 7.2% Elementary analysis (relative to anhydrous substance): Cld.: C, 41.31; H, 5.49; Gd, 22.53; N, 10.04. Fnd.: C, 41.67; H, 5.48; Gd, 22.21; N, 9.97.

Example 25 a) 10-[1-(Benzyloxycarbonylmethyl)-2-oxo-piperidin-3-yl]-1,4,7-α,α',α"-tris(isopropyl)-1,4,7-tris(benzyloxycarbonylmethyl)-1,4,7,10-tetraazacyclododecane 20.9 g (50 mmol) of 1-[1-(benzyloxycarbonylmethyl)-2-oxo-piperidin-3-yl]-1,4,7,10-tetraazacyclododecane that is described in Example 24b as an intermediate product and 60 ml (0.35 mol) of N-ethyldiisopropylamine in 200 ml of dichloromethane are added to 68.1 g (0.2 mol) of 2-(trifluoromethanesulfonyloxy)-isovaleric acid benzyl ester (Walker et al., Tetrahedron (1997), 53(43), 14591) in 400 ml of dichloromethane, and it is stirred for 6 hours under reflux and then overnight at room temperature. It is extracted three times with 500 ml of water each, and the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 36.2 g (73% of theory) of a colorless, crystalline powder Elementary analysis: Cld.: C, 70.49; H, 7.85; N, 7.09. Fnd.: C, 70.61; H, 7.83; N, 7.01.

b) 10-[1-(Carboxymethyl)-2-oxo-piperidin-3-yl]-1,4,7-α,α',α"-tris(isopropyl)-1,4,7-tris(carboxymethyl)-1,4,7,10-tetraazacyclododecane 29.6 g (30 mmol) of the title compound of Example 25a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 18.8 g (quantitative) of a colorless powder Elementary analysis: Cld.: C, 57.40; H, 8.51; N, 11.16. Fnd.: C, 57.64; H, 8.45; N, 11.09.

c) Gd Complex of 10-[1-(carboxymethyl)-2-oxo-piperidin-3-yl]-1,4,7-α,α',α"-tris(isopropyl)-1,4,7-tris(carboxymethyl)-1,4,7,10-tetraazacyclododecane 12.6 g (20 mmol) of the ligand that is described in Example 25b is dissolved in 200 ml of water and 80 ml of isopropanol and acidified by adding 5 ml of acetic acid. 3.6 g (10 mmol) of gadolinium oxide is added, and it is refluxed for 3 hours. After complexing is completed, it is set at pH 7.4 with ammonia and chromatographed on silica gel (mobile solvent: dichloromethane/methanol/ammonia: 20/20/1). The fractions that contain the product are combined and added via an IR-120® cation exchange column ($H^+$ form). The acidic eluate is freeze-dried.

Yield: 11.7 g (71% of theory) of a colorless powder. Water content (Karl-Fischer): 8.1% Elementary analysis (relative to anhydrous substance): Cld.: C, 46.08; H, 6.44; Gd, 20.11; N, 8.96. Fnd.: C, 46.34; H, 6.41; Gd, 19.99; N, 8.91.

The DY complex of 10-[1-(carboxymethyl)-2-oxo-piperidin-3-yl]-1,4,7-α,α',α''-tris(isopropyl)-1,4,7-tris(carboxymethyl)-1,4,7,10-tetraazacyclododecane is analogously obtained with use of 12.6 g (20 mmol) of the ligand that is described in Example 25b and 3.73 g (10 mmol) of dysprosium oxide instead of gadolinium oxide.

Yield: 10.8 g (66% of theory) of a colorless powder. Water content (Karl-Fischer): 7.6% Elementary analysis (relative to anhydrous substance): Cld.: C, 45.77; H, 6.40; Dy, 20.64; N, 8.90. Fnd.: C, 46.01; H, 6.46; Dy, 20.34; N, 8.91.

Example 26 a) 10-[1-(Benzyloxycarbonylmethyl)-2-oxo-piperidin-3-yl]-1,4,7-α,α',α''-tris(cyclohexyl)-1,4,7-tris(benzyloxycarbonylmethyl)-1,4,7,10-tetraazacyclododecane 20.9 g (50 mmol) of 1-[1-(benzyloxycarbonylmethyl)-2-oxo-piperidin-3-yl]-1,4,7,10-tetraazacyclododecane that is described in Example 24b as an intermediate product and 60 ml (0.35 mol) of N-ethyldiisopropylamine in 200 ml of dichloromethane are added to 76.1 g (0.2 mol) of 2-(trifluoromethanesulfonyloxy)-2-cyclohexylacetic acid benzyl ester (Qabar et al., Tetrahedron Letters (1998), 39(33), 5895) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 39.8 g (72% of theory) of a colorless, crystalline powder Elementary analysis: Cld.: C, 72.60; H, 8.09; N, 6.32. Fnd.: C, 72.89; H, 7.98; N, 6.27.

b) 10-[1-(Carboxymethyl)-2-oxo-piperidin-3-yl]-1,4,7-α,α',α''-tris(cyclohexyl)-1,4,7-tris(carboxymethyl)-1,4,7,10-tetraazacyclododecane 33.3 g (30 mmol) of the title compound of Example 26a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 22.4 g (quantitative) of a colorless powder Elementary analysis: Cld.: C, 62.63; H, 8.76; N, 9.36. Fnd.: C, 62.77; H, 8.71; N, 9.29.

c) Gd Complex of 10-[1-(carboxymethyl)-2-oxopiperidin-3-yl]-1,4,7-α,α',α''-tris(cyclohexyl)-1,4,7-tris(carboxymethyl)-1,4,7,10-tetraazacyclododecane 14.9 g (20 mmol) of the ligand that is described in Example 26b is dissolved in 150 ml of water and 150 ml of isopropanol, and it is acidified by adding 5 ml of acetic acid. 3.6 g (10 mmol) of gadolinium oxide is added, and it is refluxed for 8 hours. After complexing is completed, it is set at pH 7.4 again with ammonia and chromatographed on silica gel (mobile solvent: dichloromethane/methanol/ammonia: 20/20/1). The fractions that contain the product are combined and evaporated to the dry state. The residue is taken up with formic acid and evaporated to the dry state several times with the addition of dichloromethane and then dried in a vacuum until a constant weight is reached.

Yield: 12.9 g (68% of theory) of a colorless powder. Water content (Karl-Fischer): 7.6% Elementary analysis (relative to anhydrous substance): Cld.: C, 51.92; H, 6.93; Gd, 17.43; N, 7.76. Fnd.: C, 52.09; H, 6.88; Gd, 17.21; N, 7.77.

Example 27 a) (3-Bromo-2-oxo-piperidin-1-yl)benzoic acid benzyl ester 45.5 g (0.2 mol) of 4-aminobenzoic acid benzyl ester and 30.6 ml (0.22 mol) of triethylamine are dissolved in 200 ml of methylene chloride and added in drops within 45 minutes at 0° C. to a solution of 55.3 g (0.2 mol) of 2,5-dibromovaleric acid chloride (Okawara et al. Chem. Pharm. Bull. (1982), (30), 1225) in 200 ml of methylene chloride, and it is stirred for 18 hours at room temperature. The reaction mixture is now added in drops at 0° C. to a solution of 400 ml of aqueous 32% sodium hydroxide and 2 g of tetrabutylammonium hydrogen carbonate (about 15 minutes), and it is stirred for 30 minutes. Then, the phases are separated, and the aqueous phase is extracted three times with 200 ml of dichloromethane each. The organic phases are dried on sodium sulfate, the solution is evaporated to the dry state and chromatographed on silica gel (methylene chloride). The fractions that contain the product are combined and concentrated by evaporation.

Yield: 38.8 g (50% of theory) Elementary analysis: Cld.: C, 58.78; H, 4.67; N, 3.61. Fnd.: C, 59.01; H, 4.50; N, 3.59.

b) 10-[1-(4-Benzyloxycarbonylphenyl)-2-oxo-piperidin-3-yl]-1,4,7-α,α',α''-trimethyl-1,4,7-tris-(benzyloxycarbonylmethyl)-1,4,7,10-tetraazacyclododecane 26.6 g (68.5 mmol) of (3-bromo-2-oxo-piperidin-1-yl) benzoic acid benzyl ester is added to 31.2 g (180 mmol) of 1,4,7,10-tetraazacyclododecane, dissolved in 300 ml of chloroform, and it is stirred overnight at room temperature. 250 ml of water is added, the organic phase is separated, and it is washed twice in each case with 200 ml of water. The organic phase is dried on magnesium sulfate and evaporated to the dry state in a vacuum. The residue is chromatographed on silica gel (mobile solvent: chloroform/methanol/aqueous 25% ammonia=10/5/1). The thus obtained 1-[1-(4-benzyloxycarbonylphenyl)-2-oxo-piperidin-3-yl]-1,4,7,10-tetraazacyclododecane (27.6 g; 57.5 mmol; 84% of theory) and 60 ml (0.35 mol) of N-ethyldiisopropylamine in 200 ml of dichloromethane are added to 62.45 g (0.2 mol) of 2-(trifluoromethanesulfonyloxy)propanoic acid benzyl ester (Kitazaki et al., Chem. Pharm. Bull. (1999), 47(3), 360) in 400 ml of dichloromethane, and it is stirred for 6 hours under reflux and then overnight at room temperature. It is extracted three times with 500 ml of water, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 39.4 g (71% of theory) of a colorless, crystalline powder Elementary analysis: Cld.: C, 70.86; H, 6.99; N, 7.25. Fnd.: C, 71.11; H, 6.81; N, 7.17.

c) 10-[1-(4-Carboxyphenyl)-2-oxo-piperidin-3-yl]-1, 4,7-α,α',α"-trimethyl-1,4,7-tris(carboxymethyl)-1,4, 7,10-tetraazacyclododecane 29.0 g (30 mmol) of the title compound of Example 27b is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 18.1 g (quantitative) of a colorless powder Elementary analysis: Cld.: C, 57.51; H, 7.16; N, 11.56. Fnd.: C, 57.72; H, 7.11; N, 11.50.

d) Gd Complex of 10-[1-(4-carboxyphenyl)-2-oxo-piperidin-3-yl]-1,4,7-α,α',α"-trimethyl-1,4,7-tris (carboxymethyl)-1,4,7,10-tetraazacyclododecane 12.1 g (20 mmol) of the ligand that is described in Example 27c is dissolved in 200 ml of water and 80 ml of isopropanol, and it is acidified by adding 5 ml of acetic acid. 3.6 g (10 mmol) of gadolinium oxide is added, and it is refluxed for 3 hours. After complexing is completed, it is set at pH 7.4 again with ammonia and chromatographed on silica gel (mobile solvent: dichloromethane/methanol/ammonia: 20/20/1). The fractions that contain the product are combined and added via an IR-120® cation exchange column (H+ form). The acidic eluate is freeze-dried.

Yield: 11.4 g (72% of theory) of a colorless powder. Water content (Karl-Fischer): 7.1% Elementary analysis (relative to anhydrous substance): Cld.: C, 45.84; H, 5.31; Gd, 20.69; N, 9.22. Fnd.: C, 45.99; H, 5.26; Gd, 20.55; N, 9.21.

Example 28 a) 10-[1-(4-Benzyloxycarbonylphenyl)-2-oxo-piperidin-3-yl]-1,4,7-α,α',α"-tris(isopropyl)-1,4,7-tris(benzyloxycarbonylmethyl)-1,4,7,10-tetraazacyclododecane 24.0 g (50 mmol) of 1-[1-(4-benzyloxycarbonylphenyl)-2-oxo-piperidin-3-yl]-1,4,7,10-tetraazacyclododecane that is described in Example 27b as an intermediate product and 60 ml (0.35 mol) of N-ethyldiisopropylamine in 200 ml of dichloromethane are added to 68.1 g (0.2 mol) of 2-(trifluoromethanesulfonyloxy)-isovaleric acid benzyl ester (Walker et al., Tetrahedron (1997), 53(43), 14591) in 400 ml of dichloromethane, and it is stirred for 6 hours under reflux and then overnight at room temperature. It is extracted three times with 500 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 37.8 g (72% of theory) of a colorless, crystalline powder Elementary analysis: Cld.: C, 72.04; H, 7.58; N, 6.67. Fnd.: C, 72.32; H, 7.46; N, 6.59.

b) 10-[1-(4-Carboxyphenyl)-2-oxo-piperidin-3-yl]-1, 4,7-α,α',α"-tris(isopropyl)-1,4,7-tris(carboxymethyl)-1,4,7,10-tetraazacyclododecane 31.5 g (30 mmol) of the title compound of Example 28a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state in a vacuum.

Yield: 20.7 g (quantitative) of a colorless powder Elementary analysis: Cld.: C, 60.94; H, 8.04; N, 10.15. Fnd.: C, 60.87; H, 8.05; N, 10.11.

c) Gd Complex of 10-[1-(4-carboxyphenyl)-2-oxo-piperidin-3-yl]-1,4,7-α,α',α"-tris(isopropyl)-1,4,7-tris(carboxymethyl)-1,4,7,10-tetraazacyclododecane 13.8 g (20 mmol) of the ligand that is described in Example 28b is dissolved in 200 ml of water and 80 ml of isopropanol, and it is acidified by adding 5 ml of acetic acid. 3.6 g (10 mmol) of gadolinium oxide is added, and it is refluxed for 3 hours. After complexing is completed, it is set at pH 7.4 with ammonia and chromatographed on silica gel (mobile solvent: dichloromethane/methanol/ammonia: 20/20/1). The fractions that contain the product are combined and added via an IR-120® cation exchange column (H+ form). The acidic eluate is freeze-dried.

Yield: 12.0 g (68% of theory) of a colorless powder. Water content (Karl-Fischer): 7.5% Elementary analysis (relative to anhydrous substance): Cld.: C, 49.80; H, 6.21; Gd, 18.63; N, 8.30. Fnd.: C, 49.99; H, 6.17; Gd, 18.51; N, 8.21.

The Dy complex of 10-[1-(4-carboxyphenyl)-2-oxo-piperidin-3-yl]-1,4,7-α,α',α"-tris(isopropyl)-1,4,7-tris(carboxymethyl)-1,4,7,10-tetraazacyclododecane is analogously obtained with use of 13.8 g (20 mmol) of the ligand that is described in Example 28b and 3.73 g (10 mmol) of dysprosium oxide instead of gadolinium oxide.

Yield: 12.4 g (70% of theory) of a colorless powder. Water content (Karl-Fischer): 7.5% Elementary analysis (relative to anhydrous substance): Cld.: C, 49.50; H, 6.17; Dy, 19.13; N, 8.25. Fnd.: C, 49.77; H, 6.18; Dy, 18.89; N, 8.27.

Example 29 a) 10-[1-(4-Benzyloxycarbonylphenyl)-2-oxo-piperidin-3-yl]-1,4,7-α,α',α"-tris(cyclohexyl)-1,4,7-tris (benzyloxycarbonylmethyl)-1,4,7,10-tetraazacyclododecane 24.0 g (50 mmol) of 1-[1-(4-benzyloxycarbonylphenyl)-2-oxo-piperidin-3-yl]-1,4,7,10-tetraazacyclododecane that is described in Example 27b as an intermediate product and 60 ml (0.35 mol) of N-ethyldiisopropylamine in 200 ml of dichloromethane are added to 76.1 g (0.2 mol) of 2-(trifluoromethanesulfonyloxy)-2-cyclohexylacetic acid benzyl ester (Qabar et al., Tetrahedron Letters (1998), 39(33), 5895) in 400 ml of dichloromethane, and it is stirred for 6 hours under reflux and then overnight at room temperature. It is extracted three times with 50 ml of water each, the organic phase is dried on magnesium sulfate and evaporated to the dry state. The residue is chromatographed on silica gel (mobile solvent: dichloromethane/methanol: 20/1). The fractions that contain the product are combined and concentrated by evaporation.

Yield: 40.9 g (70% of theory) of a colorless, crystalline powder Elementary analysis: Cld.: C, 73.88; H, 7.84; N, 5.98. Fnd.: C, 74.12; H, 7.69; N, 5.89.

b) 10-[1-(4-Carboxyphenyl)-2-oxo-piperidin-3-yl]-1,4,7-α,α',α''-tris(cyclohexyl)-1,4,7-tris(carboxymethyl)-1,4,7,10-tetraazacyclododecane 35.1 g (30 mmol) of the title compound of Example 29a is dissolved in 400 ml of isopropanol, mixed with 40 ml of water, and 3 g of palladium catalyst (10% Pd/C) is added. It is hydrogenated for 8 hours at 50° C. Catalyst is filtered out, and the filtrate is evaporated to the dry state.

Yield: 24.3 g (quantitative) of a colorless powder Elementary analysis: Cld.: C, 65.24; H, 8.34; N, 8.65. Fnd.: C, 65.48; H, 8.22; N, 8.60.

c) Gd Complex of 10-[1-(4-carboxyphenyl)-2-oxo-piperidin-3-yl]-1,4,7-α,α',α''-tris(cyclohexyl)-1,4,7-tris(carboxymethyl)-1,4,7,10-tetraazacyclododecane 16.2 g (20 mmol) of the ligand that is described in Example 29b is dissolved in 150 ml of water and 150 ml of isopropanol, and it is acidified by adding 5 ml of acetic acid. 3.6 g (10 mmol) of gadolinium oxide is added, and it is refluxed for 8 hours. After complexing is completed, it is set at pH 7.4 again with ammonia and chromatographed on silica gel (mobile solvent: dichloromethane/methanol/ammonia: 20/20/1). The fractions that contain the product are combined and evaporated to the dry state. The residue is taken up with formic acid and evaporated to the dry state several times with the addition of dichloromethane and then dried in a vacuum until a constant weight is reached.

Yield: 13.6 g (68% of theory) of a colorless powder. Water content (Karl-Fischer): 7.5% Elementary analysis (relative to anhydrous substance): Cld.: C, 54.81; H, 6.69; Gd, 16.31; N, 7.26. Fnd.: C, 55.11; H, 6.57; Gd, 16.09; N, 7.24.

Examples 30–90

Examples 30–90 describe conjugates of the above-described gadolinium complexes with biomolecules. The conjugates were produced according to the following general operating instructions I-IV. The results are summarized in Table 1. Here, "AAV" stands for general operating instructions, "ACTH" stands for adrenocorticotropic hormone, and "RP-18" refers to a "reversed phase" stationary chromatography phase. The number of complexes per biomolecule was determined by means of ICP (inductively coupled plasma atomic emission spectroscopy).

General Operating Instructions (AAV) I: Albumin-amide Conjugates 3 mmol of the Gd complex acid is dissolved in 15 ml of DMF, mixed with 380 mg (3.3 mmol) of N-hydroxysuccinimide and 681 mg of dicyclohexylcarbodiimide while being cooled with ice, and preactivated for 1 hour in ice. The active ester mixture is added in drops within 30 minutes in a solution of 16.75 g (0.25 mmol) of bovine serum albumin (BSA) in 150 ml of phosphate buffer (pH 7.4) and stirred for 2 hours at room temperature. The batch solution is filtered, the filtrate is ultrafiltered with an AMICON® YM30 (cut-off 30,000 Da), the retentate is chromatographed on a Sephadex® G50-column, and the product fractions are freeze-dried.

General Operating Instructions (AAV) II: Albumin-Maleimide Conjugates 0.0438 mmol of the Gd-complex maleimide in 1 ml of DMF is added to 0.84 g (0.0125 mmol) of bovine serum albumin (BSA), dissolved in 15 ml of phosphate buffer (pH 7.4), and it is stirred for one hour at room temperature. The batch solution is filtered, the filtrate is ultrafiltered with an AMICON® YM30 (cut-off 30,000 Da), the retentate is chromatographed on a Sephadex® G50 column, and the product fractions are freeze-dried.

General Operating Instructions (AAV) III: Production of Amide Conjugates 3 mmol of the Gd-complex acid is dissolved in 15 ml of DMF, mixed with 380 mg (3.3 mmol) of N-hydroxysuccinimide and 681 mg of dicyclohexylcarbodiimide while being cooled with ice, and preactivated for 1 hour in ice. The active ester mixture is added in drops to a solution of 2.5 mmol of amine components in 15–150 ml of DMF and stirred overnight at room temperature. The batch solution is filtered and chromatographed on silica gel.

General Operating Instructions (AAV) IV: Production of Maleimido-SH Conjugates 3 mmol of the Gd-complex maleimide in 15 ml of DMF is added in drops to 2.5 mmol of SH components in 15–150 ml of DMF, and it is stirred for one hour at room temperature. The batch solution is chromatographed on silica gel.

TABLE 1

| Beispiel | Edukt Gd-Komplex (Beispiel Nr.) | konjugiert mit | (Herkunft) | AAV | Anzahl Komplexe pro Biomolekül(ICP) | Bemerkungen | Ausbeute (%) |
|---|---|---|---|---|---|---|---|
| 30 | 1 | BSA | Sigma | I | 3,7 | — | quant. |
| 31 | 2 | BSA | Sigma | I | 6,1 | — | quant. |
| 32 | 3 | BSA | Sigma | I | 2,9 | — | quant. |
| 33 | 4 | BSA | Sigma | I | 3,5 | — | quant. |
| 34 | 5 | BSA | Sigma | I | 4,2 | — | quant. |
| 35 | 6 | BSA | Sigma | I | 6,5 | — | quant. |
| 36 | 7 | BSA | Sigma | I | 5,0 | — | quant. |
| 37 | 16 | BSA | Sigma | II | 0,71 | — | quant. |
| 38 | 17 | BSA | Sigma | II | 0,55 | — | quant. |
| 39 | 8 | BSA | Sigma | I | 3,0 | — | quant. |
| 40 | 9 | BSA | Sigma | I | 4,7 | — | quant. |
| 41 | 10 | BSA | Sigma | I | 5,1 | — | quant. |
| 42 | 11 | BSA | Sigma | I | 2,7 | — | quant. |
| 43 | 12 | BSA | Sigma | I | 4,0 | — | quant. |
| 44 | 13 | BSA | Sigma | I | 3,3 | — | quant. |
| 45 | 14 | BSA | Sigma | I | 5,8 | — | quant. |
| 46 | 15 | BSA | Sigma | I | 4,6 | — | quant. |
| 47 | 18 | BSA | Sigma | I | 3,7 | — | quant. |
| 48 | 19 | BSA | Sigma | I | 4,1 | — | quant. |
| 49 | 20 | BSA | Sigma | I | 2,8 | — | quant. |
| 50 | 21 | BSA | Sigma | I | 3,5 | — | quant. |

TABLE 1-continued

| Beispiel | Edukt Gd-Komplex (Beispiel Nr.) | konjugiert mit | (Herkunft) | AAV | Anzahl Komplexe pro Biomolekül(ICP) | Bemerkungen | Ausbeute (%) |
|---|---|---|---|---|---|---|---|
| 51 | 22 | BSA | Sigma | I | 3,3 | — | quant. |
| 52 | 23 | BSA | Sigma | I | 2,9 | — | quant. |
| 53 | 24 | BSA | Sigma | I | 4,0 | — | quant. |
| 54 | 25 | BSA | Sigma | I | 3,5 | — | quant. |
| 55 | 26 | BSA | Sigma | I | 3,0 | — | quant. |
| 56 | 27 | BSA | Sigma | I | 3,9 | — | quant. |
| 57 | 28 | BSA | Sigma | I | 3,1 | — | quant. |
| 58 | 29 | BSA | Sigma | I | 3,4 | — | quant. |
| 59 | 11 | (D-Lys16)-ACTH (1–24 human) | BACHEM | I | 2,0 | — | quant. |
| 60 | 12 | ACTH (1–17) | BACHEM | I | 1,7 | — | quant. |
| 61 | 14 | H-β-Ala-Phe | BACHEM | III | 1,0 | wurde an RP-18 gereinigt | 95 |
| 62 | 8 | Anti-Inflamatory Peptide 2 | BACHEM | I | 1,0 | — | quant. |
| 63 | 9 | L-Carnosin | BACHEM | III | 1,0 | wurde an RP-18 gereinigt | 97 |
| 64 | 16 | Homoglutathion | BACHEM | IV | 1,0 | wurde an RP-18 gereinigt | 94 |
| 65 | 17 | Guanyl-Cys-OH | BACHEM | IV | 1,0 | wurde an RP-18 gereinigt | 93 |
| 66 | 8 | H-DL-d-Hydroxy-DL-Lys-OH | BACHEM | III | 1,0 | wurde an RP-18 gereinigt | 85 |
| 67 | 7 | H-β-Ala-Lys-OH | BACHEM | III | 1,0 | wurde an RP-18 gereinigt | 87 |
| 68 | 16 | H-Arg-Gly-Asp-Cys-OH | BACHEM | III | 1,0 | wurde an RP-18 gereinigt | 91 |
| 69 | 9 | H-Asp-Leu-Trp-Gln-Lys-OH | BACHEM | III | 1,0 | wurde an RP-18 gereinigt | 94 |
| 70 | 12 | H-Ala-His-Lys-OH | BACHEM | III | 2,0 | wurde an RP-18 gereinigt | 91 |
| 71 | 13 | Endothelin-2 (Human) | BACHEM | I | 0,87 | — | quant. |
| 72 | 14 | Human Serumalbumin | BACHEM | I | 5,1 | — | quant. |
| 73 | 7 | Human Serumalbumin | BACHEM | I | 3,1 | — | quant. |
| 74 | 8 | Human Serumalbumin | BACHEM | I | 2,3 | — | quant. |
| 75 | 17 | Thioguanosin | Aldrich | IV | 1,0 | wurde an RP-18 gereinigt | 96 |
| 76 | 5 | 6-Aminopenicillinsäure | Aldrich | III | 1,0 | wurde an RP-18 gereinigt | 92 |
| 77 | 11 | 4-Aminopteroylglutaminsäure | Aldrich | III | 1,0 | wurde an RP-18 gereinigt | 65 |
| 78 | 4 | 2-Amino-purinthiol | Aldrich | IV | 1,0 | wurde an RP-18 gereinigt | 94 |
| 79 | 12 | 5-Azacytidin | Aldrich | III | 1,0 | wurde an RP-18 gereinigt | 96 |
| 80 | 17 | 4,5-Diamino-2,6-dimercaptopyrimidin | Aldrich | IV | 1,0 | wurde an RP-18 gereinigt | 71 |
| 81 | 13 | Mitomycin C | Aldrich | III | 1,0 | wurde an RP-18 gereinigt | 81 |
| 82 | 12 | Muraminsäure | Aldrich | III | 1,0 | wurde an RP-18 gereinigt | 92 |
| 83 | 6 | Puromycin | SIGMA | III | 1,0 | wurde an RP-18 gereinigt | 90 |
| 84 | 11 | Doxorubicin | SIGMA | III | 1,0 | wurde an RP-18 gereinigt | 89 |
| 85 | 12 | Spectinomycin | SIGMA | III | 1,0 | wurde an RP-18 gereinigt | 88 |
| 86 | 4 | Streptomycin | SIGMA | III | 1,0 | wurde an RP-18 gereinigt | 62 |
| 87 | 14 | Neomycin B | SIGMA | III | 1,0 | wurde an RP-18 gereinigt | 52 |
| 88 | 8 | Nystatin | SIGMA | III | 1,0 | wurde an RP-18 gereinigt | 72 |
| 89 | 3 | Hygromycin | SIGMA | III | 1,0 | wurde an RP-18 gereinigt | 71 |
| 90 | 2 | Ampicillin | SIGMA | III | 1,0 | wurde an RP-18 gereinigt | 42 |

[Key to Table 1:]
Beispiel = Example
Edukt Gd-Komplex (Beispiel Nr.) = Gd-Complex Educt (Example No.)
konjugiert mit = Conjugated with
(Herkunft) = (Origin)
Anzahl Komplexe pro Biomolekul = Number of complexes per biomolecule
Bemerkungen = Remarks
Ausbeute (%) = Yield (%)
L-Carnosin = L-Carnosine TABLE 1-continued

| Beispiel | Edukt Gd-Komplex (Beispiel Nr.) | konjugiert mit | (Herkunft) AAV | Anzahl Komplexe pro Biomolekül(ICP) | Bemerkungen | Ausbeute (%) |
|---|---|---|---|---|---|---|

Homoglutathion = Homoglutathione
wurde an RP-18 gereinigt = was purified on RP-18
Thioguanosin = Thioguanosine
6-Aminopenicilinsäure = 6-Aminopenicillic acid
4-Aminopteroylglutaminsäure = 4-Aminopteroylglutamic acid
2-Amino-purinthiol = 2-amino-purinethiol
5-Azacytidin = 5-Azacytidine
4,5-Diamino-2,6-dimercaptopyrimidin = 4,5-Diamino-2,6-dimercaptopyridimidine
Muraminsäure = Muramic acid

Example 91

In this example, the relaxivities of the conjugates from Examples 30–38 were compared with the relaxivities of two comparison substances. As comparison substances, Gd-DTPA (1) with the formula:

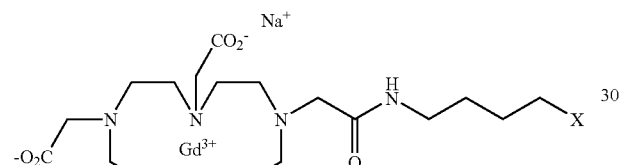

and Gd-GlyMeDOTA (2) with the formula:

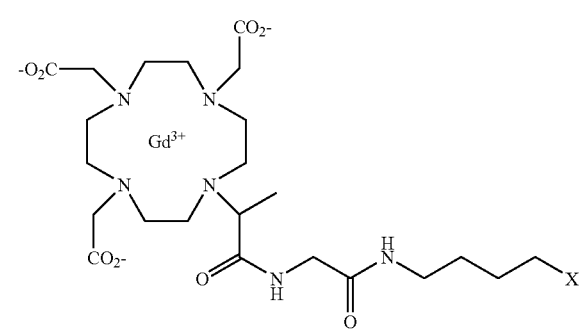

which were reacted in each case with bovine serum albumin (BSA), were used.

The measurements were made in each case in aqueous solution and in plasma at +37° C. and a frequency of 20 MHz. The results are summarized in Table 2 below, whereby the indicated relaxivities per mol of gadolinium were calculated from the measured values:

TABLE 2

| Beispiel | Gd-Komplex (aus Beispiel) | Anzahl Gd/BSA | $R_1$ ($H_2O$) (L/mmol · s) | $R_1$ (Plasma) (L/mmol · s) |
|---|---|---|---|---|
| 30 | 1 | 3.7 | 22.1 | 25.3 |
| 31 | 2 | 6.1 | 29.8 | 35.7 |
| 32 | 3 | 2.9 | 38.2 | 51.5 |
| 33 | 4 | 3.5 | 27.1 | 29.7 |
| 34 | 5 | 4.2 | 20.0 | 22.4 |
| 35 | 6 | 6.5 | 23.2 | 25.8 |
| 36 | 7 | 5.0 | 31.1 | 37.4 |
| 37 | 16 | 0.71 | 38.0 | 38.3 |
| 38 | 17 | 0.55 | 40.6 | 41.4 |
| Vergleichssubstanz 1 | Gd-DTPA | 36 | 13.39 | 13.97 |
| Vergleichssubstanz 2 | Gd-GlyMeDOTA | — | 18.3 | 20.8 |

[Key:]
Beispiel = Example
Gd-Komplex (aus Beispiel) = Gd complex (from Example)
Anzahl Gd/BSA = Gd/BSA number
Vergleichssubstanz = Comparison substance This example shows that the conjugates that are produced with the compounds according to the invention have, surprisingly enough, a higher relaxivity than the comparison substances despite their low number of gadolinium atoms per biomolecule. Compared to comparison substance 2, it was possible to increase the relaxivity by the special liganding of the macrocyclic ring.

The entire disclosures of all applications, patents and publications, cited herein and of corresponding German application No. 10135356.1, filed Jul. 20, 2001 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I

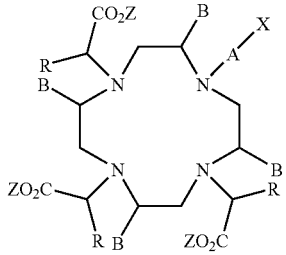

in which
Z represents a hydrogen atom and at least two Z's represent a metal ion equivalent,
B represents a hydrogen atom or a $C_{1-4}$-alkyl radical,
R represents a hydrogen atom or a straight, branched or cyclic, saturated or unsaturated $C_{1-10}$-alkyl or aryl radical, which optionally is substituted with a carboxyl group, —$SO_3H$ or —$PO_3H_2$, and whereby the alkyl chain of the $C_{1-10}$-alkyl radical optionally contains an aryl group and/or 1–2 oxygen atoms, provided that radicals B and R do not both represent hydrogen atoms simultaneously,
A represents a straight or branched, saturated or unsaturated $C_{1-30}$-hydrocarbon chain that optionally contains 1–5 oxygen atoms, 1–5 nitrogen atoms and/or 1–5 —NR' radicals, in which R' is defined as R, but is selected independently, which optionally is substituted with 1–3 carboxyl groups, 1–3 —$SO_3H$, 1–3 —$PO_3H_2$ and/or 1–3 halogen atoms, in which optionally 1–3 carbon atoms are present as carbonyl groups, whereby the chain or a portion of the chain is optionally arranged concentrically, and which is configured in such a way that X is connected via at least 3 atoms to the nitrogen to which A is bonded, and
X represents a group that is reactive such that it can participate in a reaction with a biomolecule, such that after a reaction with a biomolecule A is chemically bonded to the biomolecule,
or a salt thereof,
provided that
a) if B is a hydrogen atom and R is —$CH_2CH_2CO_2H$, A—X together are not —$CH(CO_2H)CH_2CH_2CO_2H$,
b) If B is a hydrogen atom and R is a methyl or ethyl radical, which optionally is substituted with a carboxy group, A does not represent the radical —$CH(R^4)$—CO—$NR^2U^6$—, in which $R^2$ stands for a hydrogen atom, a methyl or an ethyl radical, which optionally is substituted with 1 carboxy group, $R^4$ stands for a straight-chain, branched, saturated or unsaturated $C_1$–$C_{30}$-alkyl chain, which optionally is interrupted by 1–10 oxygen atoms, 1 phenylene group, or 1-phenylenoxy group, and/or optionally is substituted by 1–5 hydroxy groups, 1–3 carboxy groups or 1 phenyl group, and $U^6$ stands for a straight-chain, branched, saturated or unsaturated $C_1$–$C_{20}$-alkylene group that contains 1–5 imino groups, 1–3 phenylene groups, 1–3 phenylenoxy groups, 1–3 phenyleneimino groups, 1–5 amide groups, 1–2 hydrazide groups, 1–5 carbonyl groups, 1–5 ethylenoxy groups, 1 urea group, 1 thiourea group, 1–2 carboxyalkylimino groups, 1–2 ester groups, 1–10 oxygen atoms, 1–5 sulfur atoms and/or 1–5 nitrogen atoms and/or is optionally substituted by 1–5 hydroxy groups, 1–2 mercapto groups, 1–5 oxo groups, 1–5 thioxo groups, 1–3 carboxy groups, 1–5 carboxyalkyl groups, 1–5 ester groups and/or 1–3 amino groups, whereby the optionally contained phenylene groups are optionally substituted by 1–2 carboxy groups, 1–2 sulfone groups or 1–2 hydroxy groups, and
c) if B is a hydrogen atom and R is a $C_{1-4}$-alkyl radical, A does not represent the radical

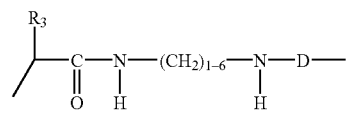

in which $R_3$ is a hydrogen atom or a $C_{1-4}$-alkyl radical,
D is a saturated or unsaturated, straight-chain or branched $C_{1-4}$-alkylene group, which optionally is interrupted or substituted with a carbonyl group, and D is bonded to X.

2. A compound according to claim 1, in which R is a hydrogen atom, a straight-chain or branched $C_{1-10}$-alkyl radical, a cyclohexyl radical, —$CH_2$—COOH, —$C(CH_3)_2$—COOH, a phenyl radical or a radical of formula —$(CH_2)_m$—$(O)_n$-(phenylene)$_p$—Y, in which m is an integer from 1 to 5, n is 0 or 1, p is 0 or 1, and y represents a hydrogen atom, a methoxy radical, a carboxyl group, —$SO_3H$ or —$PO_3H_2$.

3. A compound according to claim 2, in which if B is a hydrogen atom, R is an isopropyl radical, an isobutyl radical, a tert-butyl radical, a straight-chain or branched $C_{5-10}$-alkyl radical, a cyclohexyl radical, —$CH_2$—COOH, —$C(CH_3)_2$—COOH, a phenyl radical or a radical of formula —$(CH_2)_m$—$(O)_n$-(phenylene)$_p$—Y, in which m is an integer from 1 to 5, n is 0 or 1, p is 0 or 1, and Y represents a hydrogen atom, a methoxy radical, a carboxyl group, —$SO_3H$ or —$PO_3H_2$.

4. A compound according to claim 3, in which if B is a hydrogen atom, R is an isopropyl, cyclohexyl or phenyl radical.

5. A compound according to claim 1, in which A represents a radical A'—U, in which A' is bonded to the nitrogen atom of the macrocyclic ring and U is bonded to X, and wherein A' represents
a) a bond,
b) —$CH(CO_2H)$—,
c) a group of formula

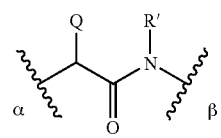

in which Q represents a hydrogen atom, a $C_{1-10}$-alkyl radical, which optionally is substituted with a carboxyl group, or an aryl radical, which optionally is substituted with a carboxyl group, a $C_{1-15}$-alkoxy group, an aryloxy group or a halogen atom, and R' is defined as R in claim 1, but is selected independently, or is d) a group of formula

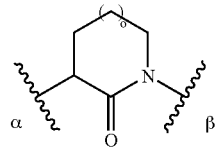

in which o is 0 or 1, and the ring optionally is annellated with a benzene ring, wherein this benzene ring, if present, is optionally substituted with a methoxy or carboxyl group, —SO$_3$H or —PO$_3$H$_2$, wherein in the groups under c) and d), the positions that are marked

are bonded to the adjacent groups, and in which position α is bonded to a nitrogen atom of the macrocyclic ring and position β is bonded to U, wherein U represents a straight or branched, saturated or unsaturated C$_{1-30}$-hydrocarbon chain that optionally contains 1–3 oxygen atoms, 1–3 nitrogen atoms and/or 1–3 —NR" radicals, in which R" is defined as R in claim 1, but is selected independently, and in which optionally 1–3 carbon atoms are present as carbonyl groups, wherein the chain or a portion of the chain is optionally arranged concentrically, provided that A' and U together are configured in such a way that X is bonded via at least 3 atoms with the nitrogen atom to which A' is bonded.

6. A compound according to claim 5, in which for A', the group of formula

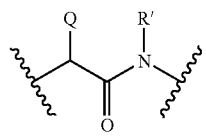

is selected from —C(CH$_3$)H—CO—NH—, —C(phenyl)H—CO—NH— and —C(p-dodecanoxy-phenyl)H—CO—NH—.

7. A compound according to claim 5, in which for A', the group of formula

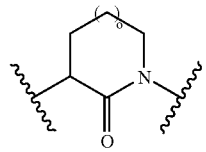

is selected from:

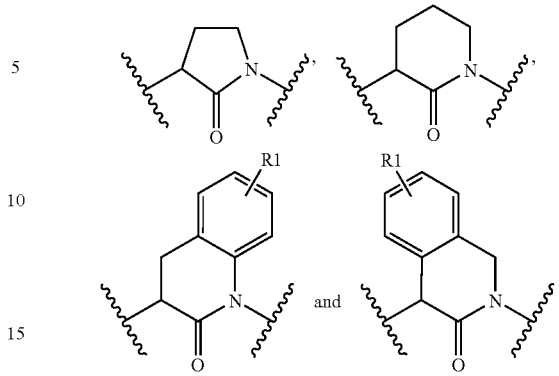

wherein R$^1$ is —OCH$_3$, —CO$_2$—H, —SO$_3$H or —PO$_3$H$_2$.

8. A compound according to claim 5, in which U is selected from —CH$_2$—, —(CH$_2$)$_5$—, —(CH$_2$)$_{10}$—, -phenylene-O—CH$_2$—, -phenylene-O—(CH$_2$)$_3$—, -phenylene-O—(CH$_2$)$_{10}$—, —CH$_2$-phenylene-, -cyclohexylene-O—CH$_2$—, -phenylene-, —C(phenyl)H—, —CH$_2$-pyridylene-O—CH$_2$—, —CH$_2$-pyridylene- and —CH$_2$—CO—NH—CH$_2$—CH$_2$—.

9. A compound of formula I

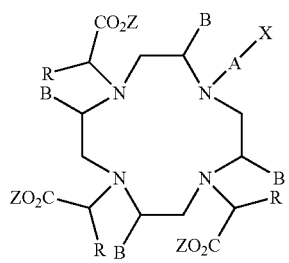

I in which

Z represents a hydrogen atom and at least two Z's represent a metal ion equivalent, B represents a hydrogen atom or a C$_{1-4}$-alkyl radical, R represents a hydrogen atom or a straight, branched or cyclic, saturated or unsaturated C$_{1-10}$-alkyl or aryl radical, which optionally is substituted with a carboxyl group —SO$_3$H or —PO$_3$H$_2$, and wherein the alkyl chain of the C$_{1-10}$-alkyl radical optionally contains an aryl group and/or 1–2 oxygen atoms, provided that radicals B and R do not both represent hydrogen atoms simultaneously, A represents a straight or branched, saturated or unsaturated C$_{1-30}$-hydrocarbon chain that optionally contains 1–5 oxygen atoms, 1–5 nitrogen atoms and/or 1–5 —NR' radicals, in which R' is defined as R, but is selected independently, which optionally is substituted with 1–3 carboxyl groups, 1–3 —SO$_3$H, 1–3 —PO$_3$H$_2$ and/or 1–3 halogen atoms, in which optionally 1–3 carbon atoms are present as carbonyl groups, wherein the chain or a portion of the chain is optionally arranged concentrically, and which is configured in such a way that X is connected via at least 3 atoms to the nitrogen to which A is bonded, and X is carboxyl, activated carboxyl, amino, isocyanate, isothiocyanate, hydrazine, semicarbazide, thiosemicarbazide, chloroacetamide, bromoacetamide, iodoacetamide, acylamino, mixed anhydrides, azide, hydroxide, sulfonyl chloride, carbodiimide and radicals of formulas

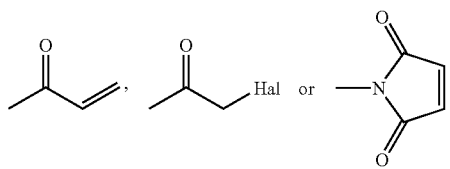

in which Hal is a halogen atom, or a salt thereof, provided that d) if B is a hydrogen atom and R is —CH$_2$CH$_2$CO$_2$H, A—X together are not —CH(CO$_2$H)CH$_2$CH$_2$CO$_2$H, e) if B is a hydrogen atom and R is a methyl or ethyl radical, which optionally is substituted with a carboxy group, A does not represent the radical —CH(R$^4$)—CO—NR$^2$U$^6$—, in which R$^2$ stands for a hydrogen atom, a methyl or an ethyl radical, which optionally is substituted with 1 carboxy group, R$^4$ stands for a straight-chain, branched, saturated or unsaturated C$_1$–C$_{30}$-alkyl chain, which optionally is interrupted by 1–10 oxygen atoms, 1 phenylene group, or 1-phenylenoxy group, and/or optionally is substituted by 1–5 hydroxy groups, 1–3 carboxy groups or 1 phenyl group, and U$^6$ stands for a straight-chain, branched, saturated or unsaturated C$_1$–C$_{20}$-alkylene group that contains 1–5 imino groups, 1–3 phenylene groups, 1–3 phenylenoxy groups, 1–3 phenylenimino groups, 1–5 amide groups, 1–2 hydrazide groups, 1–5 carbonyl groups, 1–5 ethylenoxy groups, 1 urea group, 1 thiourea group; 1–2 carboxyalkylimino groups, 1–2 ester groups, 1–10 oxygen atoms, 1–5 sulfur atoms and/or 1–5 nitrogen atoms and/or is optionally substituted by 1–5 hydroxy groups, 1–2 mercapto groups, 1–5 oxo groups, 1–5 thioxo groups, 1–3 carboxy groups, 1–5 carboxyalkyl groups, 1–5 ester groups and/or 1–3 amino groups, wherein the optionally contained phenylene groups are optionally substituted by 1–2 carboxy groups, 1–2 sulfone groups or 1–2 hydroxy groups, and f) if B is a hydrogen atom and R is a C$_{1-4}$-alkyl radical, A does not represent the radical

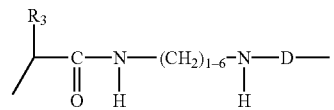

in which R$_3$ is a hydrogen atom or a C$_{1-4}$-alkyl radical, D is a saturated or unsaturated, straight-chain or branched C$_{1-4}$-alkylene group, which optionally is interrupted or substituted with a carbonyl group, and D is bonded to X.

10. A compound according to claim 9, in which the activated carboxyl group is selected from

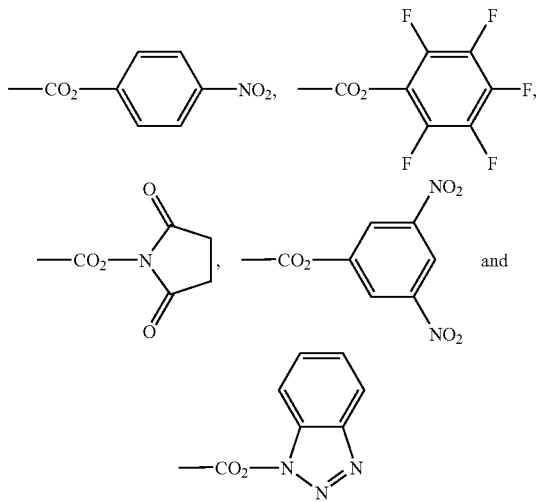

11. A compound according to claim 1 or a salt thereof, selected from 10-(4-Carboxy-1-methyl-2-oxo-3-azabutyl)-1,4,7-α,α', α"-trimethyl-1,4,7-tris(carboxymethyl)-1,4,7,10-tetraazacyclododecane;

10-(4-carboxy-1-methyl-2-oxo-3-azabutyl)-1,4,7-α,α', α"-tris(isopropyl)-1,4,7-tris(carboxymethyl)-1,4,7,10-tetraazacyclododecane;

10-(4-carboxy-1-methyl-2-oxo-3-azabutyl)-1,4,7-α,α', α"-tris(cyclohexyl)-1,4,7-tris(carboxymethyl)-1,4,7,10-tetraazacyclododecane;

10-(4-(t-butoxycarbonyl-1-phenyl-2-oxo-3-azabutyl)-1,4,7-α,α',α"-trimethyl-1,4,7-tris(carboxymethyl)-1,4,7,10-tetraazacyclododecane;

10-[α-(4-(ethoxycarbonylmethoxy)phenyl)-methoxycarbonylmethyl]-1,4,7-α,α',α"-trimethyl-1,4,7-tris(carboxymethyl)-1,4,7,10-tetraazacyclododecane;

10-[α-(4-(ethoxycarbonylpropoxy)phenyl)-methoxycarbonylmethyl]-1,4,7-α,α',α"-trimethyl-1,4,7-tris(carboxymethyl)-1,4,7,10-tetraazacyclododecane;

10-[α-(4-ethoxycarbonyldecyloxy)phenyl)-methoxycarbonylmethyl]-1,4,7-α,α',α"-trimethyl-1,4,7-tris(carboxymethyl)-1,4,7,10-tetraazacyclododecane;

10-(p-carboxybenzyl)-1,4,7-α,α',α"-trimethyl-1,4,7-tris(carboxymethyl)-1,4,7,10-tetraazacyclododecane;

10-(p-carboxybenzyl)-1,4,7-α,α',α"-tris(isopropyl)-1,4,7-tris(carboxymethyl)-1,4,7,10-tetraazacyclododecane;

10-(p-carboxybenzyl)-1,4,7-α,α',α"-tris(cyclohexyl)-1,4,7-tris(carboxymethyl)-1,4,7,10-tetraazacyclododecane;

10-(p-carboxybenzyl)-1,4,7-α,α',α"-triphenyl-1,4,7-tris(carboxymethyl)-1,4,7,10-tetraazacyclododecane;

10-(4-(t-butoxycarbony-1-phenyl-2-oxo-3-azabutyl)-1,4,7-α,α',α"-triphenyl-1,4,7-tris(carboxymethyl)-1,4,7,10-tetraazacyclododecane;

10-(4-carboxy-2-oxo-3-azabutyl)-1,4,7-α,α',α"-tris(isopropyl)-1,4,7-tris(carboxymethyl)-1,4,7,10-tetraazacyclododecane;

10-(4-carboxy-2-oxo-3-azabutyl)-1,4,7-α,α',α"-tris(cyclohexyl)-1,4,7-tris(carboxymethyl)-1,4,7,10-tetraazacyclododecane;

10-[8-(N-maleimido)-1-methyl-2,5-dioxo-3,6-diazaoctyl]-1,4,7-α,α',α''-tris-(isopropyl)-1,4,7-tris(carboxymethyl)-1,4,7,10-tetraazacyclododecane; and 10-[8-N-maleimido)-1-methyl-2,5-dioxo-3,6-diazaoctyl]-1,4,7-α,α',α''-tris(cyclohexyl)-1,4,7-tris(carboxymethyl)-1,4,7,10-tetraazacyclododecane, wherein in each of the above compounds at least two hydrogens are replaced by a metal ion equivalent and a metal ion complex of 10-(4-carboxy-1-methyl-2-oxo-3-azabutyl)-2,5,8,11-tetramethyl-1,4,7,10-tetraazacyclododecane-1,4,7-triacetic acid.

12. A compound according to claim 1, in which at least two of radicals Z stand for a metal ion equivalent of a radioactive or paramagnetic element of atomic numbers 21–29, 31, 32, 37–39, 42–44, 46, 47, 49, 58–71, 75, 77, 82 or 83.

13. A process for preparing a compound according to claim 1,

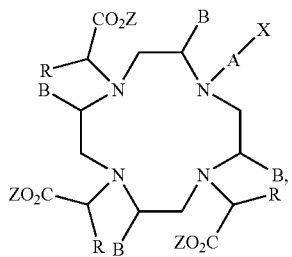

provided that B and R do not represent hydrogen atoms simultaneously and if B is a hydrogen atom and R is a C$_{1-4}$-alkyl radical, A does not represent the radical

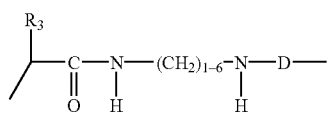

in which R$_3$ is a hydrogen atom or a C$_{1-4}$-alkyl radical, D is a saturated or unsaturated, straight-chain or branched C$_{1-4}$-alkylene group, which optionally is interrupted or substituted with a carbonyl group, and D is bonded to X, comprising reacting a compound of formula II

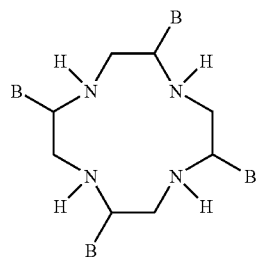

in which B is defined as in claim 1, with Nu—A—X' and Nu—CH(R)—CO$_2$—Z' optionally after protective groups for the nitrogen atoms are introduced, wherein A and R are defined as in claim 1, and Nu is a nucleofuge, X' stands for X or a protected form of X, and X is defined as in claim 1, and Z' stands for a hydrogen atom, a metal ion equivalent or a protective group for carboxyl, then the optionally present protective groups are removed, and optionally reacted with at least one metal oxide or metal salt and optionally then still present acid hydrogen atoms are completely or partially substituted in the thus obtained complexes by cations of inorganic and/or organic bases, amino acids or amino acid amides.

14. A compound according to claim 1, wherein B is methyl, ethyl or iso-propyl.

15. A compound according to claim 1, wherein B is hydrogen and R is C$_{5-10}$alkyl or aryl radical which optionally is substituted with a carboxyl group —SO$_3$H or —PO$_3$H$_2$, and wherein the alkyl chain of the C$_{5-10}$-alkyl radical optionally contains an aryl group and/or 1–2 oxygen atoms.

16. A compound according to claim 1, wherein B is hydrogen and R is pentyl, hexyl, cyclohexyl, heptyl, octyl, nonyl or decyl.

17. A compound according to claim 1, wherein A is configured in such a way that X is connected via at least 4 atoms to the nitrogen to which A is bonded.

18. A compound according to claim 1, wherein A is a group of one of the following formulae

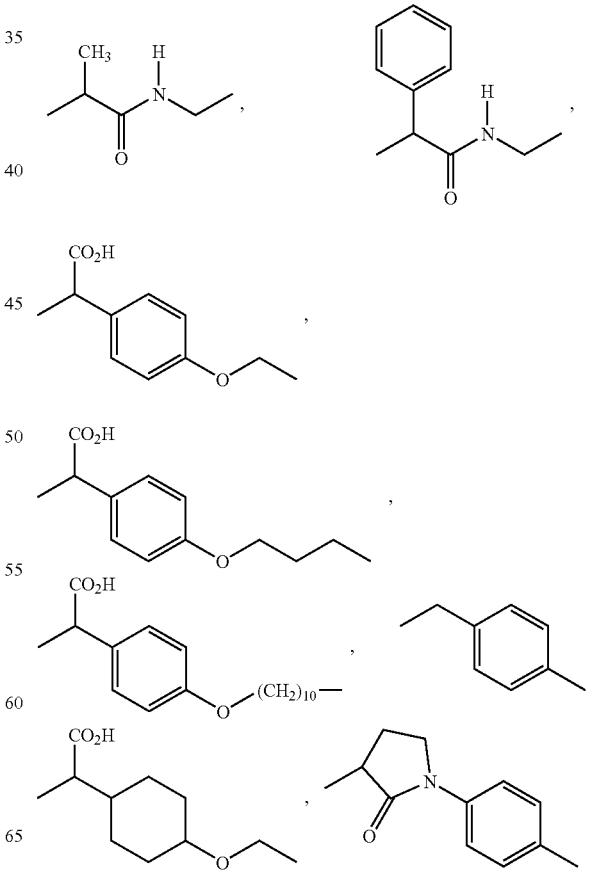

-continued

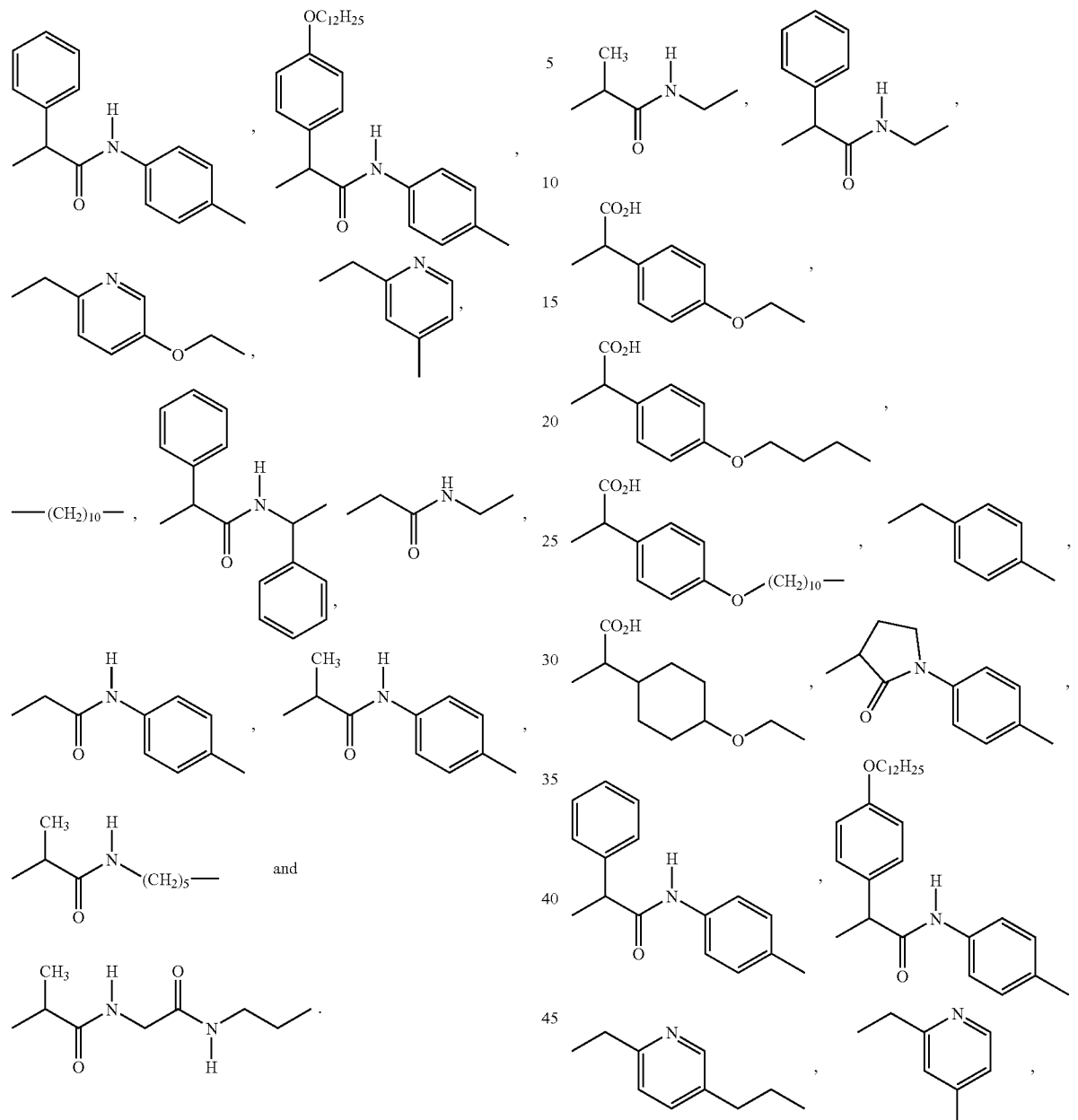

19. A compound according to claim 9, wherein B is methyl, ethyl or iso-propyl.

20. A compound according to claim 9, wherein B is hydrogen and R is $C_{5-10}$ alkyl or aryl radical which optionally is substituted with a carboxyl group —$SO_3H$ or —$PO_3H_2$, and wherein the alkyl chain of the $C_{5-10}$-alkyl radical optionally contains an aryl group and/or 1–2 oxygen atoms.

21. A compound according to claim 9, wherein B is hydrogen and R is pentyl, hexyl, cyclohexyl, heptyl, octyl, nonyl or decyl.

22. A compound according to claim 9, wherein A is configured in such a way that X is connected via at least 4 atoms to the nitrogen to which A is bonded.

23. A compound according to claim 9, wherein A is a group of one of the following formulae -continued
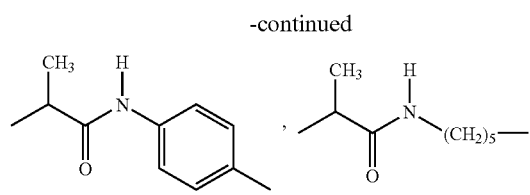
and
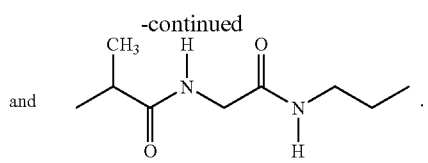
* * * * *

UNITED STATES PATENT AND TRADEMARK OFFICE
CERTIFICATE OF CORRECTION

PATENT NO. : 7,164,016 B2 Page 1 of 1
APPLICATION NO. : 10/198046
DATED : January 16, 2007
INVENTOR(S) : Johannes Platzek It is certified that error appears in the above-identified patent and that said Letters Patent is hereby corrected as shown below:

Column 55, line 24 reads "whereby", should read -- wherein --

Column 55, line 36 reads "whereby", should read -- wherein --

Column 56, line 5 reads "whereby", should read -- wherein --

Signed and Sealed this

First Day of April, 2008

JON W. DUDAS
*Director of the United States Patent and Trademark Office*